(12) United States Patent
Leyden et al.

(10) Patent No.: US 7,837,689 B2
(45) Date of Patent: Nov. 23, 2010

(54) PLATE HOLDER ASSEMBLY HAVING BONE PLATE SEATING CONFIRMATION ARRANGEMENT

(75) Inventors: Matthew V. Leyden, St. Paul, MN (US); Jeffrey B. Waffensmith, North Oaks, MN (US); Timothy A. Bachman, St. Paul, MN (US); Matthew S. Wallace, Fort Wayne, IN (US); Marc E. Ruhling, Goshen, IN (US); Anthony J. Metzinger, Winona Lake, IN (US); Charles D. Christie, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 221 days.

(21) Appl. No.: 11/904,504

(22) Filed: Sep. 27, 2007

(65) Prior Publication Data

US 2009/0088806 A1    Apr. 2, 2009

(51) Int. Cl.
*A61B 17/80* (2006.01)
(52) U.S. Cl. .................. 606/86 B; 606/62; 606/280; 606/99
(58) Field of Classification Search .......... 606/62–68, 606/70–71, 280–299, 86 B, 86 R, 87–89, 606/104
See application file for complete search history.

(56) References Cited

U.S. PATENT DOCUMENTS

| | | | |
|---|---|---|---|
| 2,526,959 A | 10/1950 | Lorenzo | |
| 3,554,193 A | 1/1971 | Konstantinou et al. | |
| 4,438,762 A * | 3/1984 | Kyle | 606/65 |
| 4,465,065 A | 8/1984 | Gotfried | |
| 5,324,292 A | 6/1994 | Meyers | |
| 5,755,721 A * | 5/1998 | Hearn | 606/96 |
| 5,951,554 A * | 9/1999 | Holmes | 606/104 |
| 6,916,323 B2 * | 7/2005 | Kitchens | 606/86 R |
| 6,926,720 B2 * | 8/2005 | Castaneda | 606/98 |
| 7,056,322 B2 | 6/2006 | Davison et al. | |

(Continued)

FOREIGN PATENT DOCUMENTS

WO   WO 2005/084559   9/2006

(Continued)

OTHER PUBLICATIONS

Colored copy of DePuy Orthopaedics' brochure entitled "Captured Hip Screw System Surgical Technique"; Published at least as early as Sep. 26, 2007; Nineteen (19) pages.

(Continued)

*Primary Examiner*—Eduardo C Robert
*Assistant Examiner*—Steven J Cotroneo
(74) *Attorney, Agent, or Firm*—Maginot, Moore & Beck

(57) ABSTRACT

An assembly includes a plate holder having a body. The assembly further includes a stop structure movable in relation to the body between a first location and a second location. In addition, the assembly includes a bone plate assembly including (i) a bone plate having a plurality of fastener openings defined therein, the bone plate being attached to the body, and (ii) a fastener guide. One of the bone plate and the fastener guide includes a channel, and the other of the bone plate and the fastener guide includes a projection configured to be received in the channel.

12 Claims, 18 Drawing Sheets

U.S. PATENT DOCUMENTS

| | | | |
|---|---|---|---|
| 7,431,731 B2* | 10/2008 | Kitchens | 606/281 |
| 2006/0095044 A1* | 5/2006 | Grady et al. | 606/96 |
| 2006/0116679 A1* | 6/2006 | Lutz et al. | 606/69 |
| 2006/0122604 A1* | 6/2006 | Gorhan et al. | 606/69 |
| 2007/0162011 A1 | 7/2007 | Leyden et al. | |
| 2008/0275447 A1* | 11/2008 | Sato et al. | 606/65 |

FOREIGN PATENT DOCUMENTS

| | | |
|---|---|---|
| WO | WO 2005/084560 | 9/2006 |

OTHER PUBLICATIONS wisdomking.com web site: *Plastic 180° Pocket Goniometer—121005*; http://www.wisdomking.com/product55238.html. Downloaded from website on Sep. 9, 2007 (2 pages).

Amazon.com website: "*goniometer*", http://www.amazon.com/exedobidos/search-handle-url/index=blended&field-keywords=go. . . Downloaded from website on Sep. 9, 2007 (4 pages).

* cited by examiner

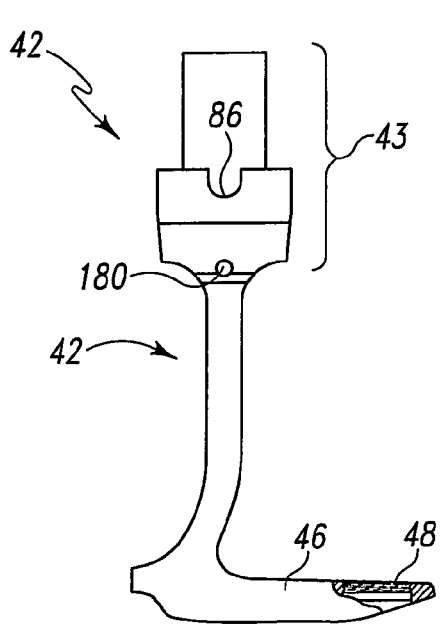
Fig. 9
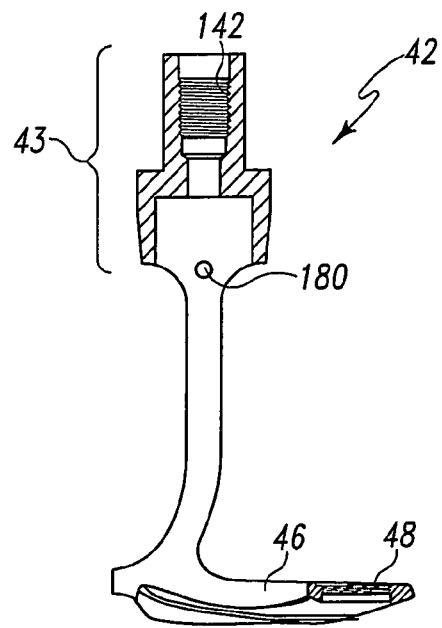
Fig. 10
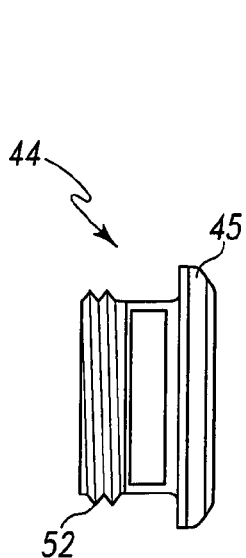
Fig. 11
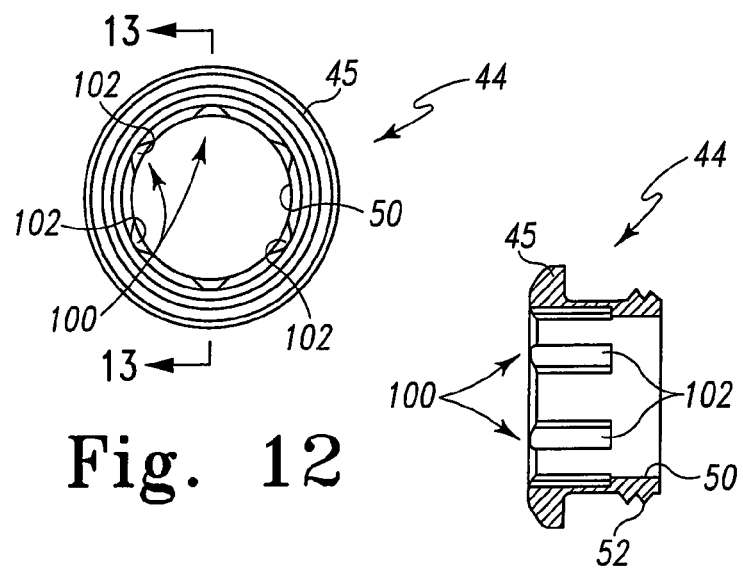
Fig. 12
Fig. 13

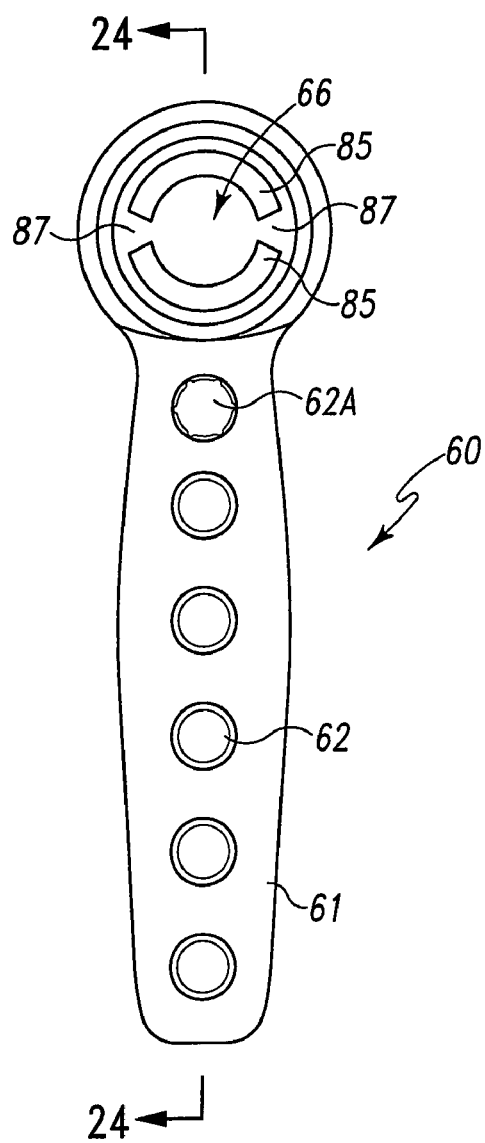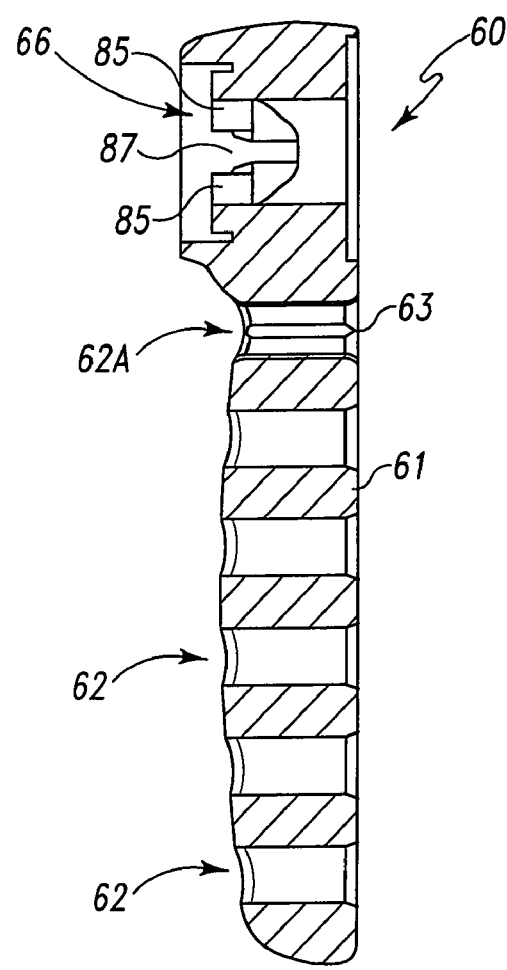
Fig. 23
Fig. 24

PLATE HOLDER ASSEMBLY HAVING BONE PLATE SEATING CONFIRMATION ARRANGEMENT

CROSS REFERENCE TO RELATED APPLICATIONS

Cross reference is made to copending (i) U.S. patent application Ser. No. 11/904,414, entitled "Plate Holder Assembly having Movable Guide Component" by Richard Kyle, Jeffrey Waffensmith, Matthew Leyden, Tim Bachman, Matthew Wallace, and Marc Ruhling, (ii) U.S. patent application Ser. No. 11/904,476, entitled "Plate Holder and Bone Plate Arrangement" by Matthew Leyden, Jeffrey Waffensmith, Matthew Wallace, and Marc Ruhling, (iii) U.S. patent application Ser. No. 11/904,399, entitled "Apparatus for Measuring an Angle of a Guide Wire Relative to a Bone" by Stuart R. Grant, Anthony J. Metzinger, David A. Hawkes, and Andrew H. Berthusen, and (iv) U.S. patent application Ser. No. 11/904,520, entitled "Guide Assembly for Use in a Medical Procedure" by Matthew Leyden, Aaron Bisek, David A. Hawkes, Marc Ruhling, Jeffrey Waffensmith, and Matthew Wallace, which are assigned to the same assignee as the present invention, and which are filed concurrently herewith. The disclosures of the four above-identified patent applications are herein totally incorporated by reference in their entirety.

BACKGROUND

The present disclosure relates generally to the reduction of a hip fracture by the placement of a bone plate and associated bone fasteners with instrumentation.

A procedure regularly performed by orthopedic surgeons is the reduction of a hip fracture caused by trauma. The site of this type of fracture typically exists at the proximal portion of the femur below the head. In order to reduce a fracture of this type, an elongated lag screw is threadingly advanced into the shaft, neck, and head of the femur, and secured to a bone plate. Cortical screws are used to secure the bone plate to the femur distal to the fracture site. Tightening of the lag screw compresses the bone fragments together and facilitates healing of the femur. Many devices have been designed for this type of reduction including the devices disclosed in U.S. Pat. Nos. 4,438,762, 3,554,193, and 2,526,959, the disclosures of which are incorporated herein by reference in their entirety.

During the above procedure, it is necessary to advance a bone plate into a seated arrangement with a lag screw barrel through which the lag screw extends. When the hip fracture reduction procedure is performed in a minimally invasive manner, visual confirmation of proper seating of the bone plate with the lag screw barrel may be difficult, if not impossible. Indeed, in a minimally invasive hip reduction procedure, the bone plate and lag screw barrel may be covered in large part by a patient's body tissues such as skin and soft tissue. It would be desirable if the implants and instrumentation used in a hip fracture procedure would facilitate confirmation of proper seating of the bone plate with the lag screw barrel. Moreover, it would be desirable if such implants and instrumentation that would facilitate confirmation of proper seating of the bone plate with the lag screw barrel were relatively easy to use.

What is needed therefore is apparatus that facilitate confirmation of proper seating of a bone plate with a lag screw barrel during a hip fracture reduction procedure. What is also needed is apparatus that facilitate confirmation of proper seating of a bone plate with a lag screw barrel during a minimally invasive hip fracture reduction procedure. What is further needed is such apparatus that are easy to use.

SUMMARY

In accordance with one embodiment of the disclosure, there is provided an assembly that includes a plate holder having a body. The assembly further includes a stop structure movable in relation to the body between a first location and a second location. In addition, the assembly includes an actuator movable between a first position and a second position. Movement of the actuator from the first position to the second position causes movement of the stop structure from the first location to the second location.

Pursuant to another embodiment of the disclosure, there is provided an assembly that includes a plate holder having a body. The assembly further includes a stop structure movable in relation to the body between a first location and a second location. The assembly also includes a bone plate assembly including (i) a bone plate having a plurality of fastener openings defined therein, the bone plate being attached to the body, and (ii) a fastener guide. One of the bone plate and the fastener guide includes a channel, and the other of the bone plate and the fastener guide includes a projection configured to be received in the channel.

BRIEF DESCRIPTION OF THE DRAWINGS

FIG. 9 is a side elevational view of the plate holder of the instrument assembly of FIG. 5;

FIG. 10 is a cross sectional view of the plate holder of the instrument assembly of FIG. 5;

FIG. 11 is a side elevational view of the coupling component of the instrument assembly of FIG. 5;

FIG. 12 is a top elevational view of the coupling component of the instrument assembly of FIG. 5;

FIG. 13 is a cross sectional view of the coupling component taken along the line 13-13 of FIG. 12;

FIG. 23 is a bottom elevational view of a guide component of the instrument assembly of FIG. 5;

FIG. 24 is a cross sectional view of the guide component taken along the line 24-24 of FIG. 23;

DESCRIPTION OF THE PREFERRED EMBODIMENTS

Figure 1:
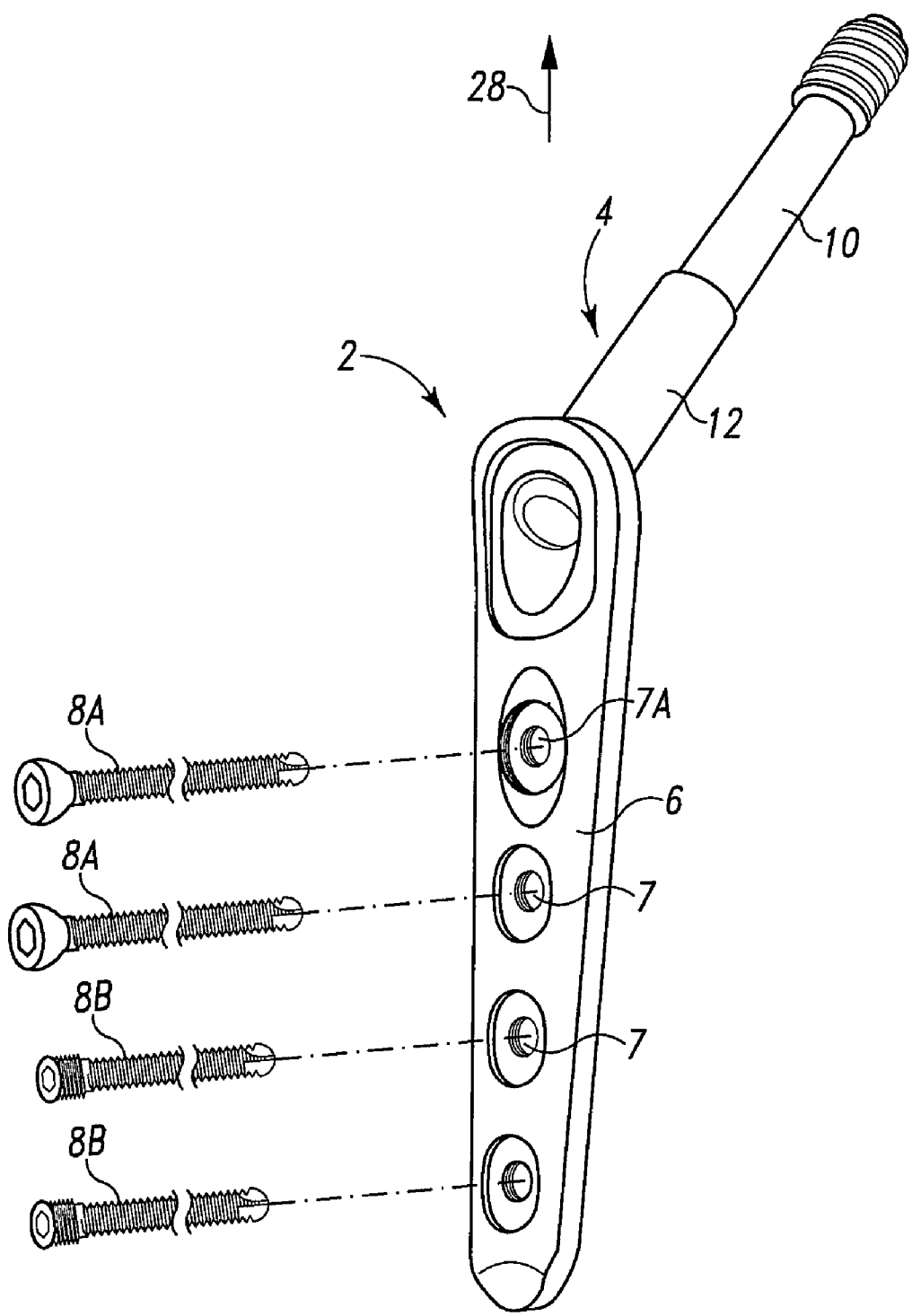
FIG. 1 is a perspective view of an implant assembly which is implanted in a minimally invasive manner according to the present disclosure.
Figure 2A:
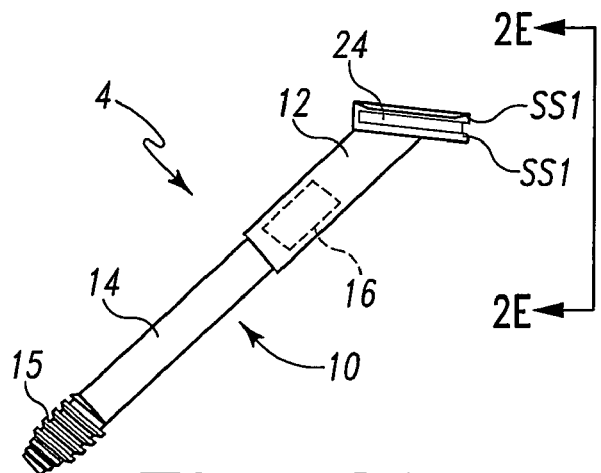
FIG. 2A is a side elevational view of the lag screw assembly of the implant assembly of FIG. 1.
Figure 2B:
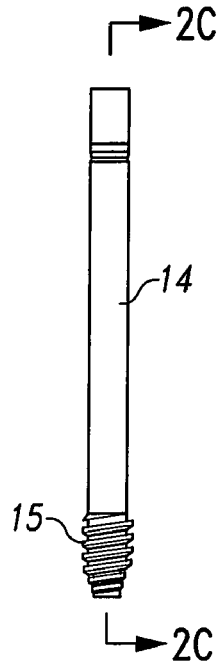
FIG. 2B is a side elevational view of the lag screw component of the lag screw assembly of FIG. 2A.
Figure 2D:
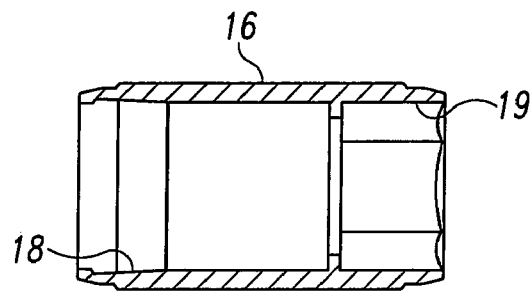
FIG. 2D is a cross sectional view of the sleeve of the lag screw assembly of FIG. 2A.
Figure 2E:
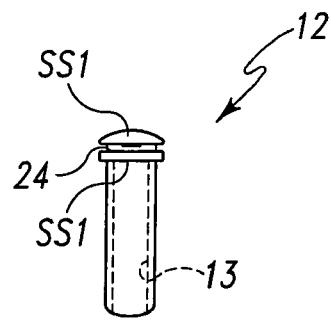
FIG. 2E is a side elevational view of the fastener guide taken along the line 2E-2E of FIG. 2A.
Figure 2C:
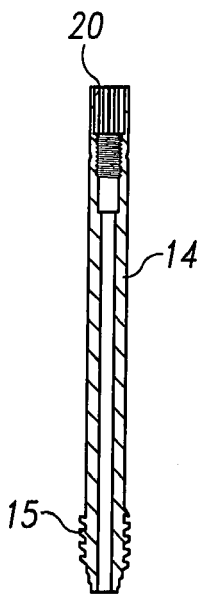
FIG. 2C is a cross sectional view of the lag screw component taken along the line 2C-2C of FIG. 2B.

While the assembly described herein is susceptible to various modifications and alternative forms, specific embodiments thereof have been shown by way of example in the drawings and will herein be described in detail. It should be understood, however, that there is no intent to limit the assembly to the particular forms disclosed, but on the contrary, the intention is to cover all modifications, equivalents, and alternatives falling within the spirit and scope of the invention as defined by the appended claims.

Instrumentation and Implant Components

Described below are instrumentation and implant components that facilitate reduction of a hip fracture in a minimally invasive manner. As shown in FIGS. 1, 2A-2E, and 3A-3D, the implant components include an implant assembly 2 that includes a lag screw assembly 4, a bone plate 6, and a plurality of bone screws 8A, 8B. The bone screws 8A include two non-locking cortical bone screws, while the bone screws 8B include two locking cortical bone screws. Alternatively, other combinations of locking screws 8A and non-locking screws 8B may be used with the bone plate 6. Further, instead of using a combination of locking and non-locking screws, all locking screws 8B may used with the bone plate 6, or alternatively all non-locking screws 8A may be used with the bone plate 6.

Figure 3A:
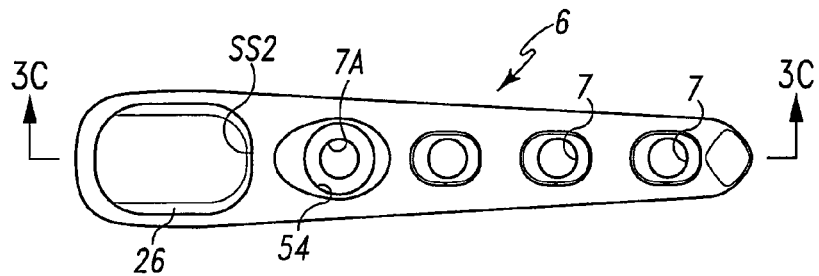
FIG. 3A is a top elevational view of the bone plate of the implant assembly of FIG. 1.
Figure 3B:
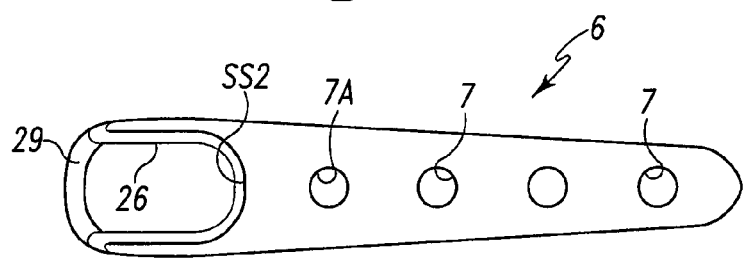
FIG. 3B is a bottom elevational view of the bone plate of the implant assembly of FIG. 1.
Figure 3C:
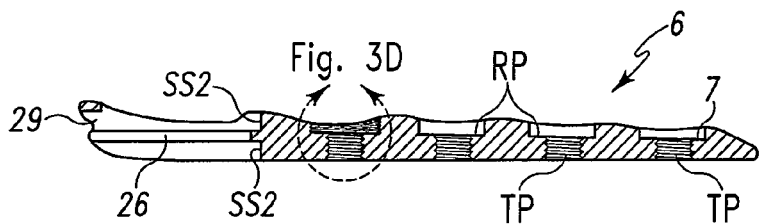
FIG. 3C is a cross sectional view of the bone plate taken along the line 3C-3C of FIG. 3A.
Figure 3D:
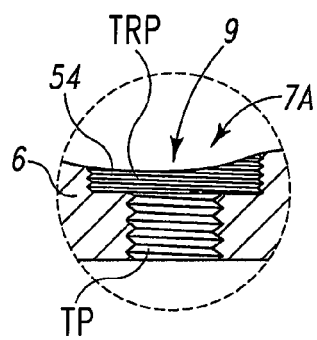
FIG. 3D is an enlarged, fragmentary, cross sectional view of the bone plate showing the portion of FIG. 3C that is encircled and identified as FIG. 3D.

The bone plate 6 has defined therein a plurality of fastener openings 7, 7A configured to receive the bone screws 8A, 8B. Each of the fastener openings 7 include a recess portion RP and a threaded portion TP that are aligned with each other as shown in FIG. 3C. The fastener opening 7A includes a threaded recess portion TRP and a threaded portion TP that are aligned with each other as shown in FIG. 3D. The threaded recess portion TRP defines a set of internal threads 54. The structure of the bone plate 6 that defines the threaded recess portion TRP creates a coupling component 9.

The lag screw assembly 4 includes a lag screw 10 and a fastener guide or barrel 12. The fastener guide 12 defines a passage 13 in which the lag screw 10 is partially positioned. The lag screw 10 includes a lag screw component 14 and a sleeve 16 that are rotatably attached together. The lag screw component 14 has defined therein a plurality of threads 15. The sleeve 16 is configured to slide axially within the passage 13 of the fastener guide 12, but is prevented from being able to rotate in relation to the fastener guide 12 by mating structure (not shown) of the sleeve 16 and fastener guide 12. The sleeve 16 has defined therein a passage 18 that defines a hexagonal shaped recess 19. The lag screw component 14 is freely rotatable in relation to the sleeve 16. However, when a keying mechanism (not shown) is positioned within the recess 19 of the sleeve 16 and a hexagonal-shaped recess 20 of the lag screw component 14, the sleeve 16 and the lag screw component 14 are rotationally or angularly locked together. In other words, rotation of the sleeve 16 causes rotation of the lag screw component 14. Thus, when the keying mechanism is positioned within the recess 19 and the recess 20, the lag screw component 14 is rotationally or angularly locked in relation to the fastener guide 12 since the sleeve 16 is prevented rotating in relation to the fastener guide 12 as discussed above. However, the lag screw component 14 is able to slide axially in relation to the passage 13 of the fastener guide 12.

Alternatively, the sleeve 16 may be permanently fixed in relation to the lag screw component 14 so that, after assembly of these components, rotation of the sleeve 16 causes rotation of the lag screw component 14. An alternative lag screw assembly that may be utilized in the lag screw assembly 4 is the lag screw assembly disclosed in U.S. Patent Application Publication No. US2007/0162011, having a U.S. application Ser. No. 11/303,833, the disclosure of which is herein incorporated by reference in its entirety.

The bone plate 6 cooperates with the lag screw assembly 4 to assume the configuration shown in FIG. 1. In particular, the fastener guide 12 defines a channel 24. The channel 24 is preferably U-shaped. The bone plate 6 defines an access opening 29 through which the fastener guide 12 may advance. The bone plate 6 includes a projection 26. The projection 26 is preferably U-shaped. The projection 26 of the bone plate 6 is configured to be received within the channel 24 of fastener guide 12. In order to mate the bone plate 6 with the lag screw assembly 4, the bone plate 6 is advanced in the direction indicated by arrow 28 (see FIG. 1) so that the fastener guide 12 passes through the access opening 29 of the bone plate whereby the projection 26 of the bone plate is received within the channel 24 of the fastener guide. Continued advancement of the bone plate 6 in relation to the fastener guide 12 in the direction of arrow 28 results in a seating surface SS1 of the fastener guide 12 contacting a seating surface SS2 of the bone plate 6. When seating surface SS1 is positioned in contact with the seating surface SS2, the bone plate 6 and the fastener guide 12 are in an assembled state.

Figure 4:
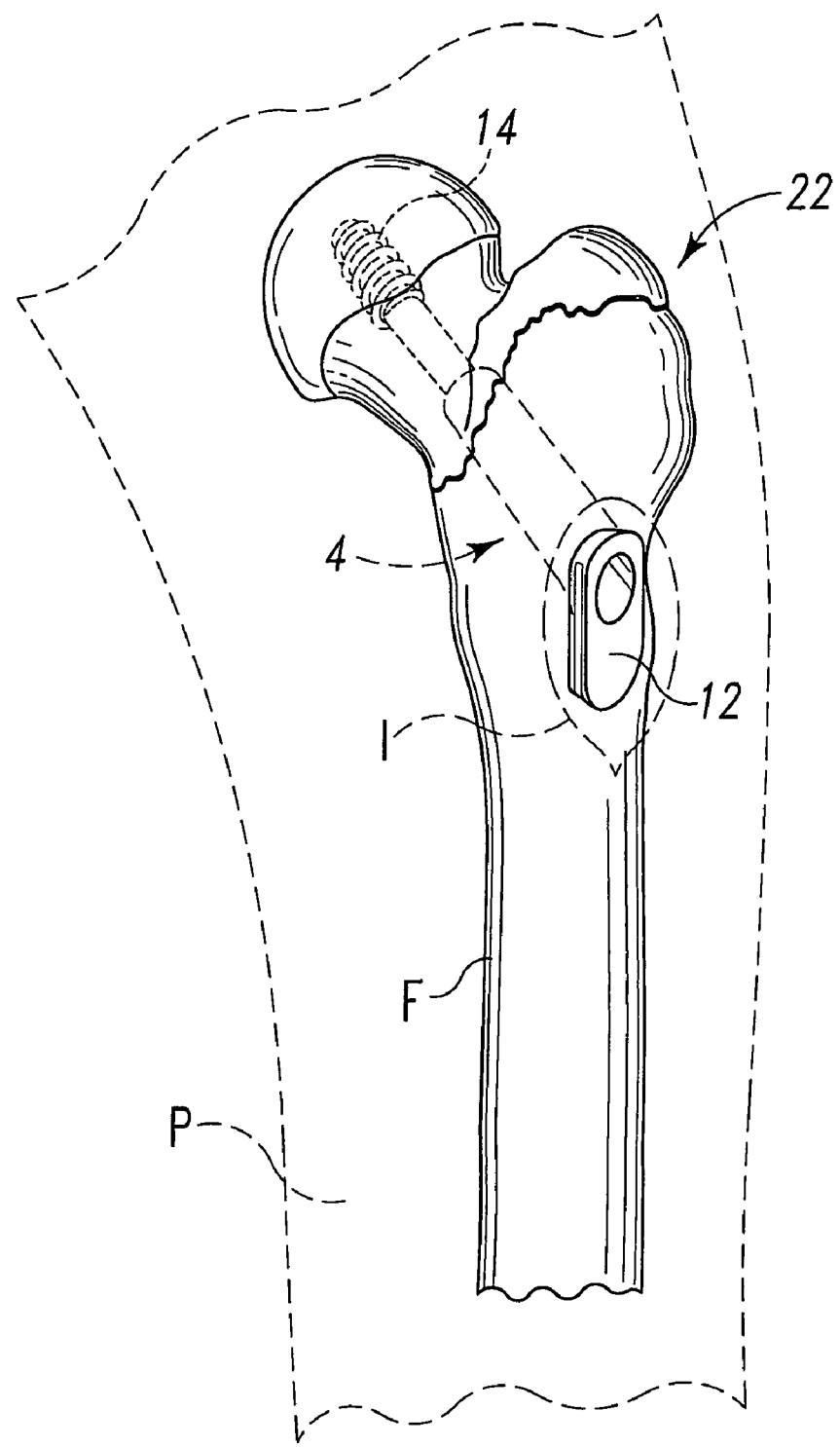
FIG. 4 is a perspective view of the lag screw assembly of FIG. 2A implanted in a femur of a patient according to the present disclosure, with the lag screw assembly being partially visually exposed through an incision in a patient.

At a particular stage during a hip fracture reduction procedure, the lag screw assembly 4 is secured within a femoral head, neck, and shaft of a femur F of a patient P as shown in FIG. 4. The lag screw assembly 4 is partially visually exposed through an incision I in the patient P as shown in FIG. 4. The femur F has a fracture 22 defined therein as shown in FIG. 4.

Figure 5:
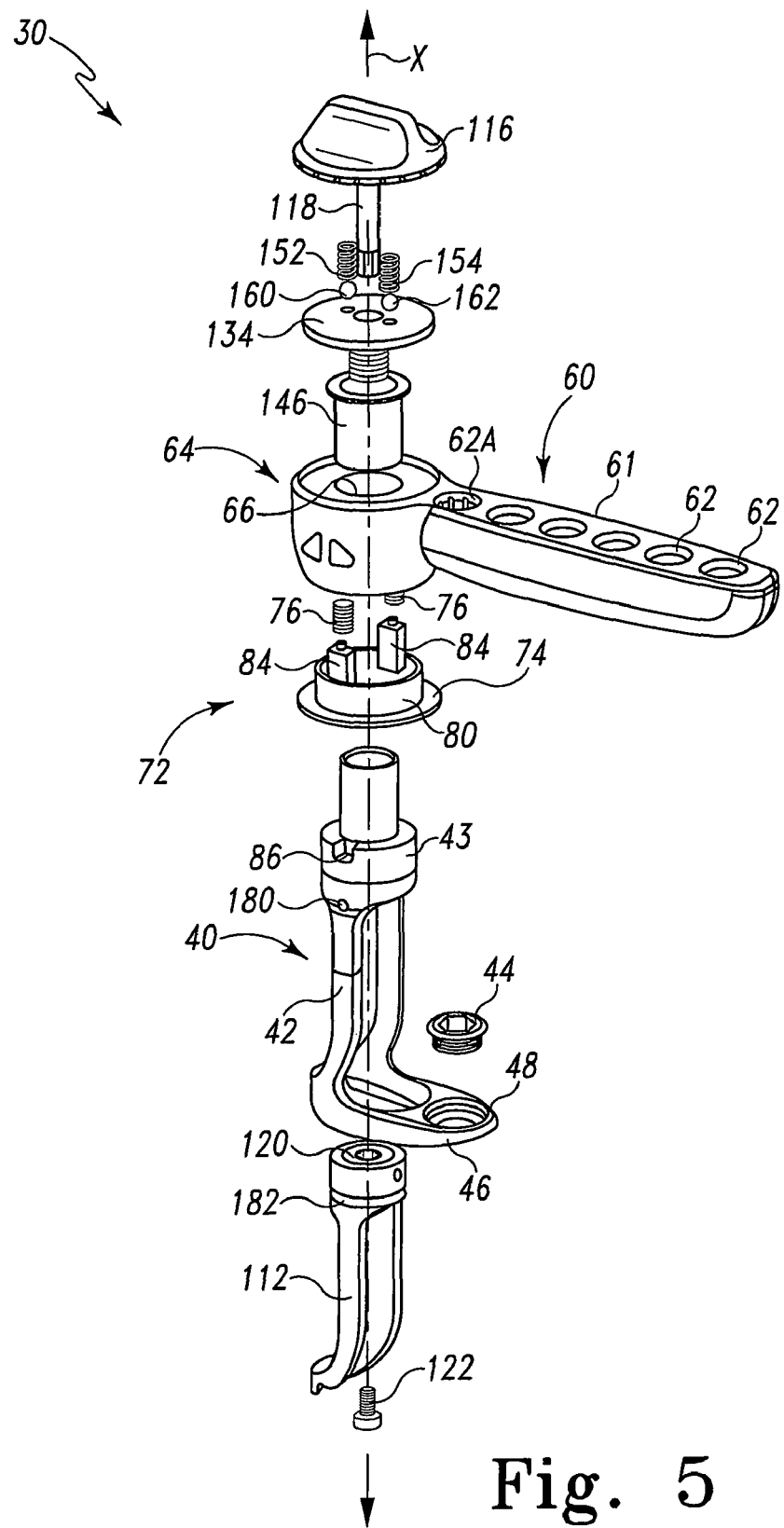
FIG. 5 is an exploded, perspective view of an instrument assembly (with the implant assembly not shown) that is used to implant the implant assembly of FIG. 1 in the patient in a minimally invasive manner according to the present disclosure.
Figure 6:
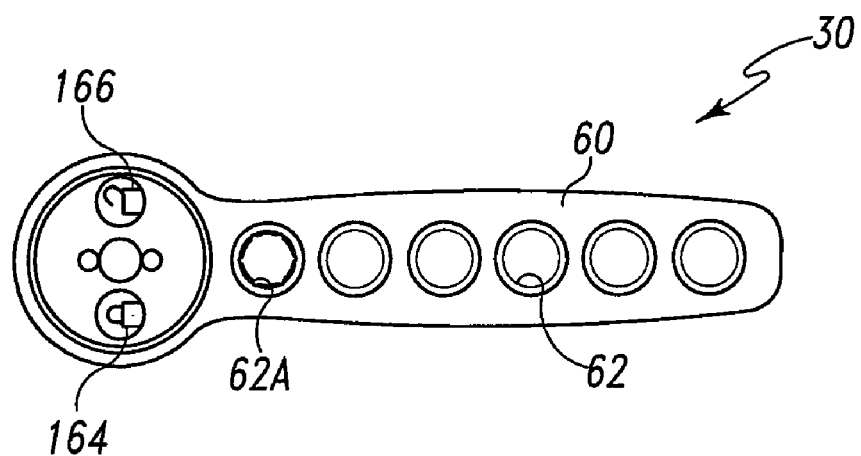
FIG. 6 is a top elevational view of the instrument assembly of FIG. 5, with the knob of the instrument assembly removed for clarity of viewing.
Figure 7:
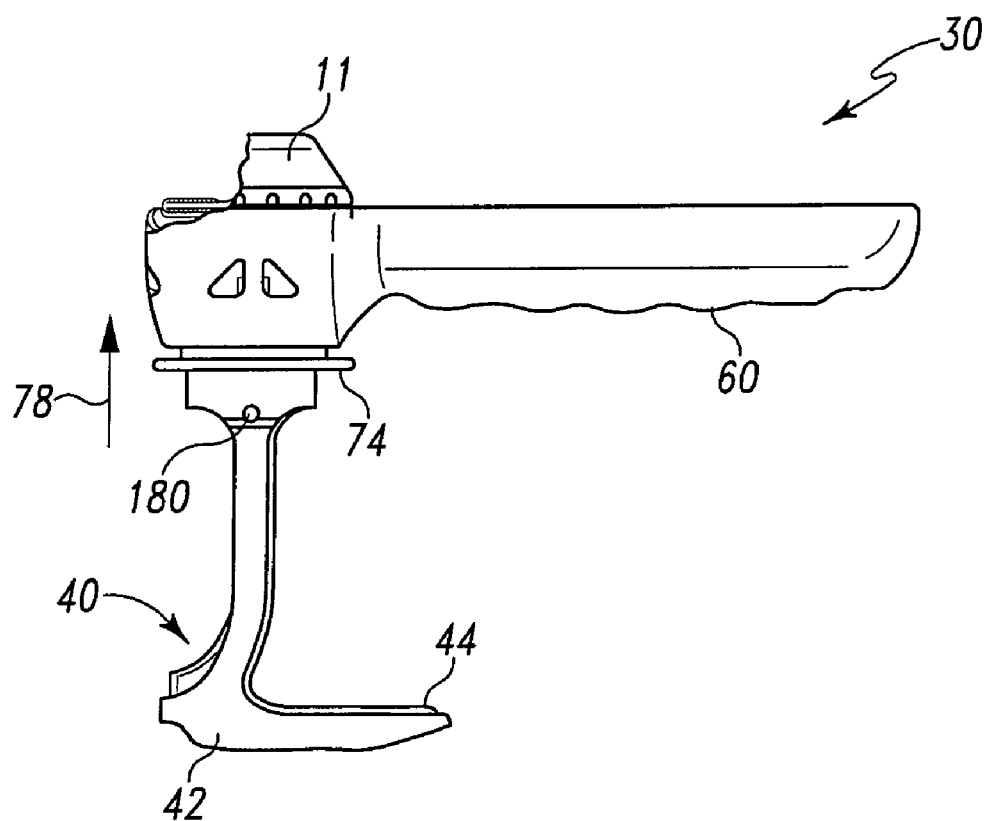
FIG. 7 is a side elevational view of the instrument assembly of FIG. 5, with the implant assembly not shown.
Figure 8:
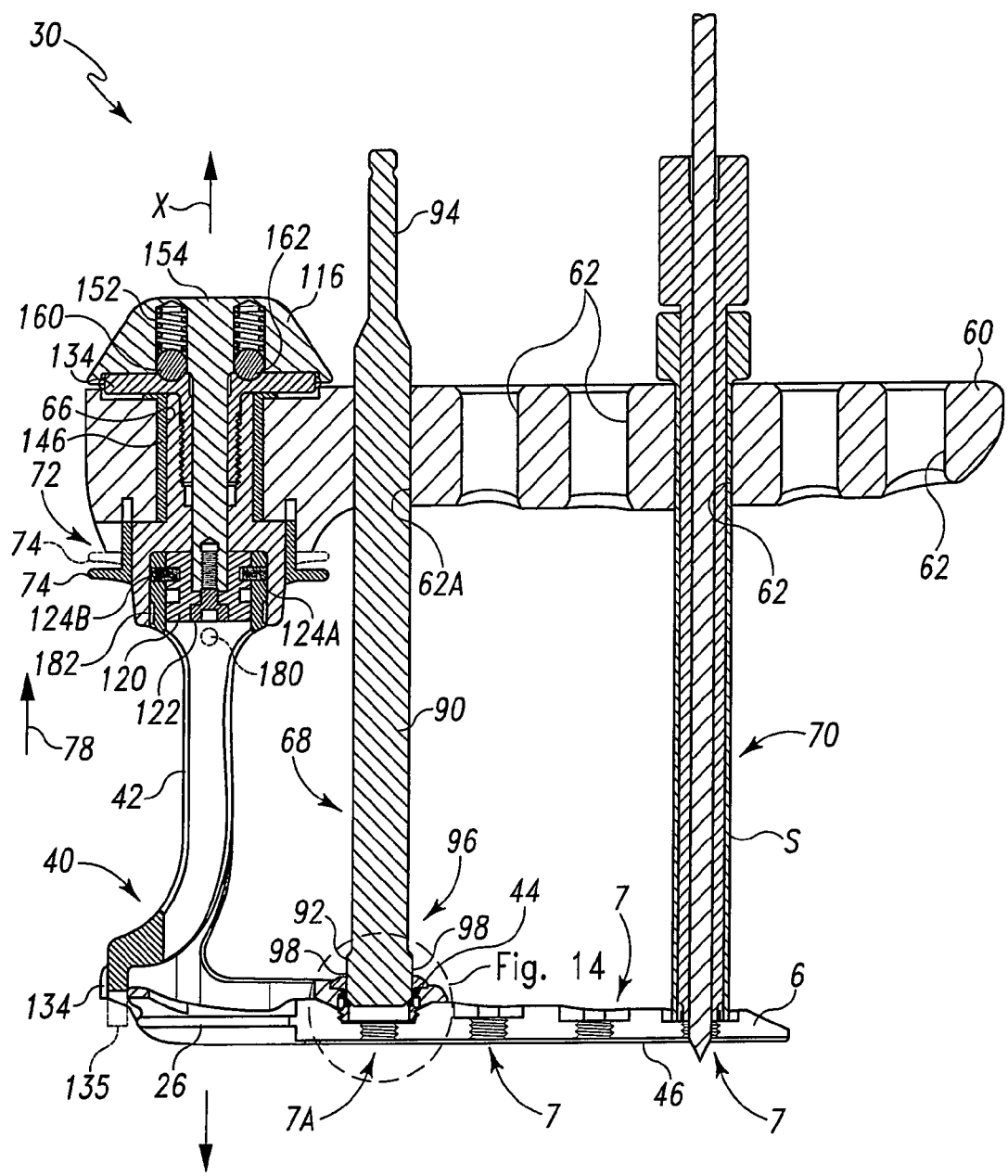
FIG. 8 is a cross sectional view of the instrument assembly of FIG. 5, with the implant assembly shown.

Turning now to FIGS. 5-7, there is shown an instrument assembly 30 that is used to facilitate implantation of the bone plate 6 and the bone screws 8A, 8B of the implant assembly 2 into the patient P. FIG. 8 also shows the instrument assembly 30, and a couple of other devices supported thereby.

Figure 14:
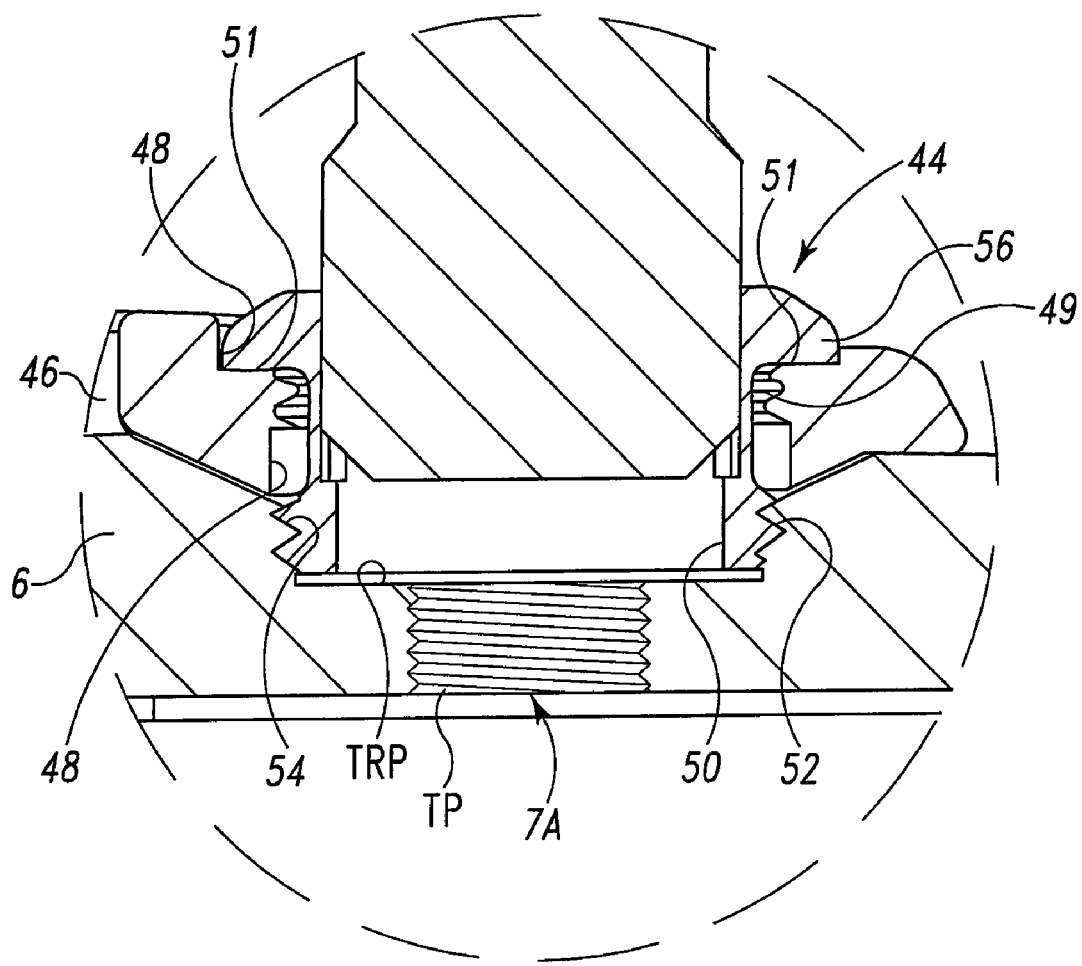
FIG. 14 is an enlarged, fragmentary, cross sectional view of the instrument assembly showing the portion of FIG. 8 that is encircled and identified as FIG. 14.

The instrument assembly 30 includes a plate holder 40 having a body 42 and a coupling component 44 rotatably supported by the body 42. The body 42 is also shown in FIGS. 9-10, while the coupling component 44 is also shown in FIGS. 11-13. The body 42 includes a foot portion 46 that defines a passage 48. The body 42 further includes a neck 43. The foot portion 46 includes a set of internal threads 49 located within the passage 48 as shown in FIG. 14. The coupling component 44 has defined therein a passage 50 extending therethrough. The coupling component 44 includes a flange 45 and a set of external threads 52 that is configured to meshingly engage with the set of internal threads 49 of the foot portion 46. The set of external threads 52 of the coupling component 44 is also configured to meshingly engage with a set of internal threads 54 defined in the bone plate 6 as shown in FIG. 14.

In order to assemble the coupling component 44 to the foot portion 46, the coupling component 44 is advanced into the passage 48 of the foot portion until the set of external threads 52 of the coupling component 44 contact the set of internal threads 49 of the foot portion 46. Thereafter, the coupling component 44 is rotated so that the set of external threads 52 meshing engagement with the set of internal threads 49 of the foot portion 46. Continued rotation of the coupling component 44 in relation to the foot portion 46 results in advancement of the set of external threads 52 through the set of internal threads 49. After the set of external threads 52 are advanced through the set of internal threads 49, the coupling component 44 is rotatably attached to the foot portion 46. In this assembled state, the coupling component 44 is able to rotate freely in relation to the foot portion 46. Further, the coupling 44 is able to move a distance axially within the passage 48, but is prevented from becoming detached from the foot portion 46. Indeed, upward movement of the coupling component 44 in relation to the foot portion 46 is limited by interaction of the set of external threads 52 of the coupling component and the set of internal threads 49 of the foot portion. Also, downward movement of the coupling component 44 in relation to the foot portion 46 is limited by interaction of the flange 56 of the coupling component and a shoulder 51 of the foot portion which is located in the passage 48.

Note that when the set of external threads 52 of the coupling component 44 are mated with the set of internal threads 54 of the bone plate 6, the bone plate 6 is secured to the foot portion 44 of the plate holder 40. Also note that when the set of external threads 52 of the coupling component 44 are mated with the set of internal threads 54 of the bone plate 6, the passageway 50 of the coupling component 44 is aligned with the fastener opening 7A of the bone plate 6.

Figure 15:
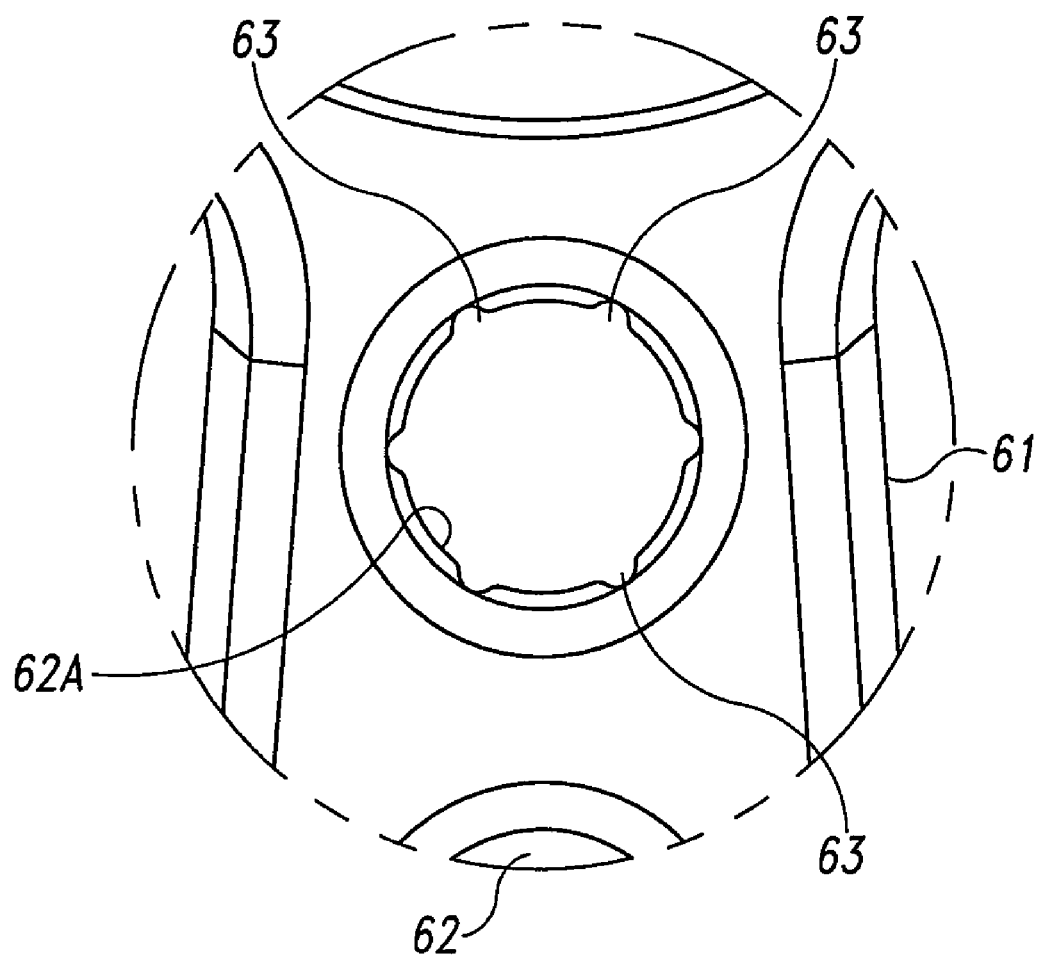
FIG. 15 is an enlarged, fragmentary, top elevational view of the guide component of the instrument assembly of FIG. 5.

As shown in FIGS. 5-8, the instrument assembly 30 further includes a guide component 60 that is pivotably secured to the body 42 of the plate holder 40. The guide component 60 includes a handle portion 61 having defined therein a plurality of guide holes 62, 62A. The handle portion further defines a plurality of peripheral slots 63 that are located in the guide hole 62A as shown in FIGS. 5 and 15. The guide component 60 further includes an end portion 64 that includes a cavity 66 defined therein as shown in FIGS. 23-24.

Figure 16:
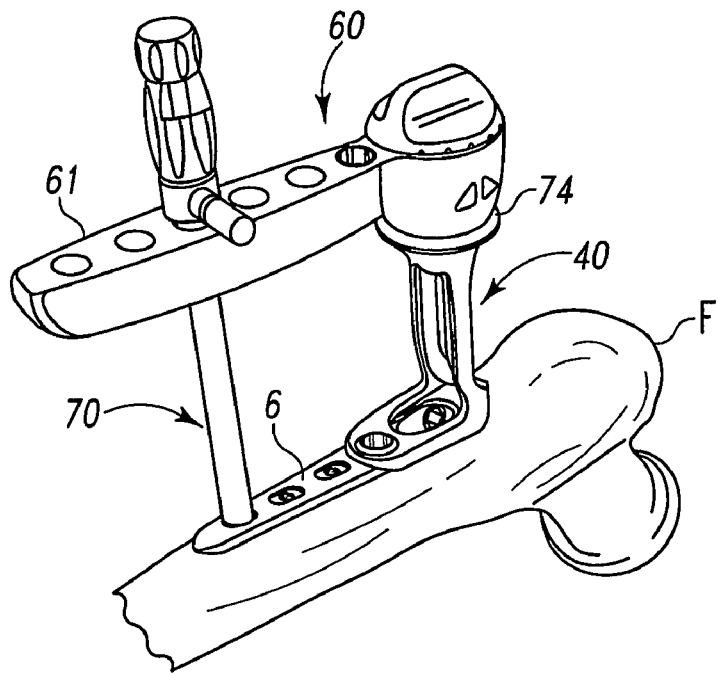
FIG. 16 is a perspective view of the instrument assembly of FIG. 5 (with the implant assembly attached thereto) and being used to implant the implant assembly in a femur according to the present disclosure, with the femur and the implant assembly being shown removed from the body of a patient P for clarity of viewing.
Figure 17:
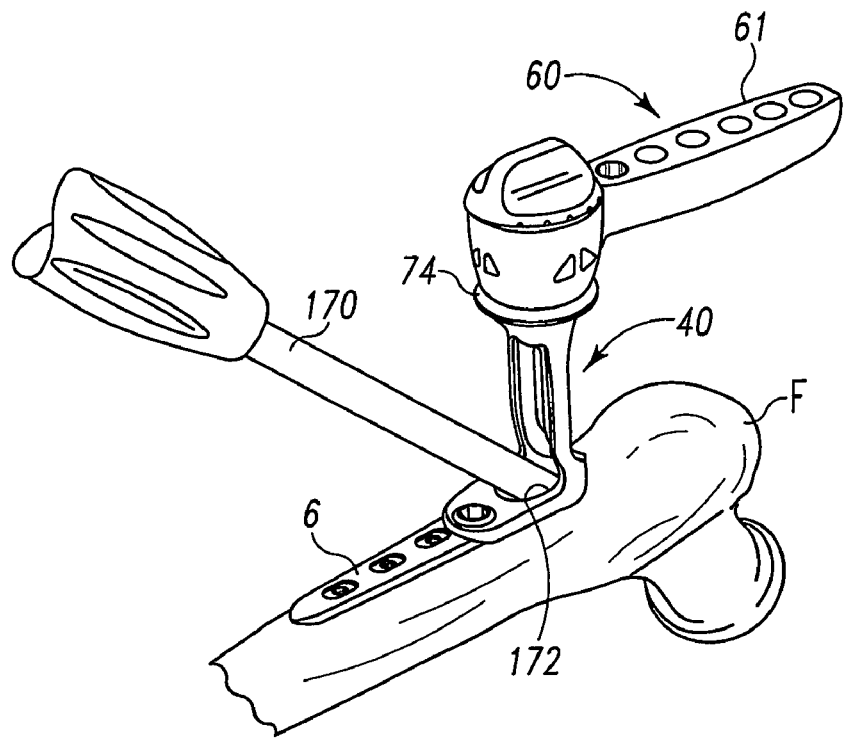
FIG. 17 is another perspective view of the instrument assembly of FIG. 5 (with the implant assembly attached thereto) and being used to implant the implant assembly in a femur according to the present disclosure, with the femur and the implant assembly being shown removed from the body of a patient P for clarity of viewing.
Figures 18, 19:
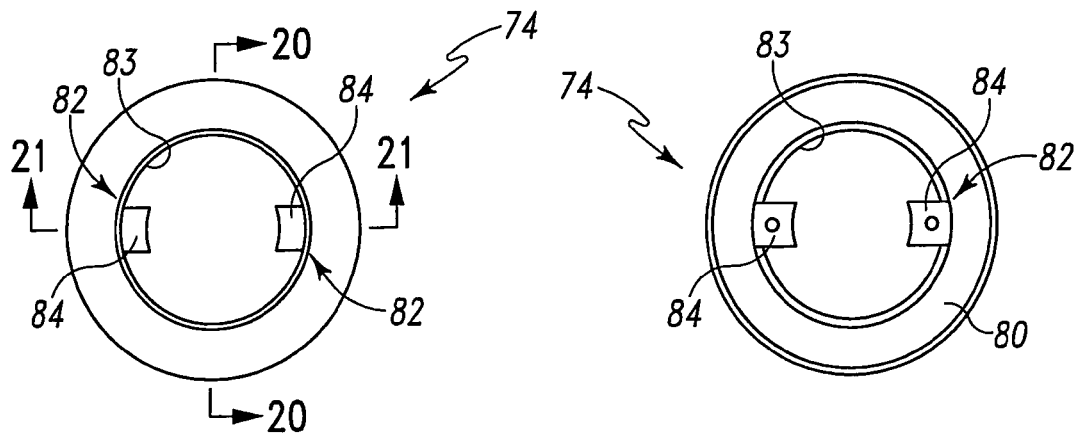
FIG. 18 is a bottom elevational view of an actuator of the instrument assembly of FIG. 5.
FIG. 19 is a top elevational view of the actuator of FIG. 18.
Figures 20, 21:
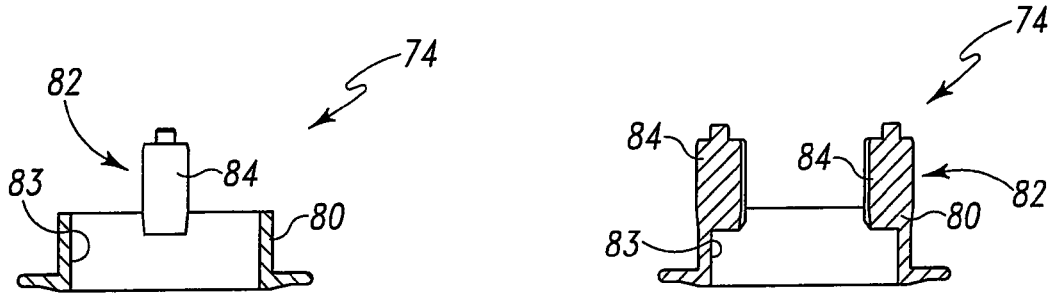
FIG. 20 is a cross sectional view of the actuator taken along the line 20-20 of FIG. 18.
FIG. 21 is a cross sectional view of the actuator taken along the line 21-21 of FIG. 18.

Since the guide component 60 is pivotably connected to the plate holder 40, the guide component 60 is movable in relation to the body 42 of the plate holder 40 between a first position shown in FIG. 16 (see also FIGS. 7-8) and a second position shown in FIG. 17. The guide component 60 pivots about an axis X. (See FIGS. 5 and 8.) Pivoting the guide component 60 180° about the axis X causes the guide component 60 to move from its first position (see FIG. 16) to its second position (see FIG. 17).

When the guide component 60 is located at its first position in relation to the plate holder 40 (see FIG. 16), the plurality of guide holes 62, 62A are respectively aligned with the plurality of fastener openings 7, 7A. For example, as shown in FIG. 8, the left most guide hole 62A is aligned with the left most fastener opening 7A so that an elongate instrument (e.g. a driver 68) may be advanced through the guide hole 62A and present its working end at the fastener opening 7A. Further, for example, as shown in FIG. 8, the fourth guide hole 62 (from the left) is aligned with the fourth fastener opening 7 (from the left) so that an elongate instrument (e.g. a drill assembly 70) may be advanced through the guide hole 62 and present its working end at the fastener opening 7. When the guide component 60 is located at its second position in relation to the plate holder 40 (see FIG. 17), the plurality of guide holes 62, 62A are respectively misaligned with the plurality of fastener openings 7, 7A. Indeed, advancing elongate instruments 68, 70 respectively through the guide holes 62, 62A would not result in the working ends of the elongate instruments being respectively presented at the fastener openings 7, 7A.

Moreover, as can be seen from FIGS. 16 and 17, when the guide component 60 is positioned at its first position in relation to the plate holder 40 (see FIG. 16), the handle portion 61 is positioned over the bone plate 6. On the other hand, when the guide component 60 is positioned at its second position in relation to the plate holder 40 (see FIG. 17), the handle portion 61 is not positioned over the bone plate 6. Positioning of the guide component 60 at its second position (see FIG. 17) facilitates visibility of the bone plate 6 and surrounding area. Moreover, positioning of the guide component 60 at its second position (see FIG. 17) facilitates access of instruments and other devices to the bone plate 6 and surrounding area.

Figure 22:
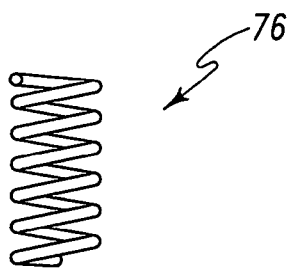
FIG. 22 is a side elevational view of a spring 76 of the instrument assembly of FIG. 5.

The instrument assembly 30 further includes a locking mechanism 72 that is configured to lock the guide component 60 in relation to the body 42 of the plate holder 40 at its first position as shown in FIG. 16, and at its second position as shown in FIG. 17. The locking mechanism 72 includes an actuator 74 that is partially located in the cavity 66 of the guide component 60. The actuator 74 is movable between a lower position (shown in solid in FIG. 8), and an upper position (shown in phantom in FIG. 8). The locking mechanism 72 includes a plurality of springs 76 configured to bias the actuator 74 toward its lower position. (See FIG. 8.) The springs 76 have an identical configuration with respect to each other, and one spring 76 is shown in FIG. 22. The springs 76 are located in the cavity 66 of the guide component 60. Within the cavity 66, the springs 76 are interposed between the actuator 74 and the guide component 60. In order to move the actuator 74 from its lower position to its upper position against the spring bias of the springs 76, force is applied to the actuator in the direction of arrow 78 thereby urging the actuator upwardly until the actuator 74 contacts a lower surface of the guide component 60. Thereafter, in order to move the actuator 74 from its upper position to its lower position, the upwardly applied force is removed thereby allowing the springs 76 to urge the actuator 74 downwardly to its lower position.

When the actuator 74 is positioned in its lower position, the guide component 60 is locked in relation to the body 42 of the plate holder 40 at its first position (shown in FIG. 16). Thereafter, an upward force is applied to the actuator 74 in the direction of arrow 78 thereby moving the actuator from its lower position (shown in solid in FIG. 8) to its upper position (shown in phantom in FIG. 8). When the actuator 74 is positioned in its upper position, the guide component 60 is free to rotate in relation to the body 42 of the plate holder. Force is then applied to the guide component 60 so that the guide component 60 pivots 180° about the axis X causing the guide component 60 to move from its first position (shown in FIG. 16) to its second position (shown in FIG. 17). Thereafter, the upward force is removed from the actuator 74 thereby allowing the springs 76 to urge the actuator 74 downwardly to its lower position. When the actuator 74 is positioned in its lower position, the guide component 60 is locked in relation to the body 42 of the plate holder 40 at its second position (shown in FIG. 17).

As shown in FIGS. 18-21, the actuator 74 includes a body 80 and a blocking structure 82 supported by the body 80. The body 80 defines a passage 83 therethrough. The blocking structure 82 includes a number of detents 84 attached to the body 80. The body 42 of the plate holder 40 has defined therein a number of detent recesses 86. (See FIGS. 5 and 9.) As shown in FIGS. 23-24, the guide component 60 includes a number of internal walls 85 that are positioned within the passage 66. The internal walls 85 define a number of slots 87.

When the instrument assembly 30 is in an assembled state, the body 80 of the actuator 74 is positioned around the neck 43 of the plate holder 40 so that the neck 43 extends through the passage 83 of the body 80 of the actuator 74 as shown in FIG. 8. The detents 84 are located within the slots 87 of the guide component 60. Thus, the actuator 74 is able to move in the direction of axis X since the detents 84 are able slide axially within the slots 87, however, the internal walls 85 of the guide component 60 prevent rotation of the actuator 74 in relation to the guide component 60. Thus, the actuator 74 is rotationally fixed in relation to the guide component 60.

When the actuator 74 is positioned at its lower position (shown in solid in FIG. 8), the blocking structure 82 is located in the number of detent recesses 86. In particular, one detent 84 is positioned in one detent recess 86, while another detent 84 is positioned in another detent recess 86. As a result, rotation of the actuator 74 in relation to the body 42 of the plate holder 40 is prevented when the actuator 74 is positioned at its lower position. And since the actuator 74 is rotationally fixed in relation to the guide component 60, the guide component 60 is prevented from rotating in relation to the body 42 of the plate holder 40 when the actuator 74 is positioned at its lower position.

In contrast, when the actuator 74 is positioned at its upper position (shown in phantom in FIG. 8), the blocking structure 82 is spaced apart from the number of detent recesses 86. In particular, both detents 84 are spaced apart from both detent recesses 86. Therefore, rotation of the actuator 74 in relation to the body 42 of the plate holder 40 is allowed when the actuator 74 is positioned at its upper position. Thus, the guide component 60 is allowed to be rotated in relation to the body 42 of the plate holder 40 when the actuator 74 is positioned at its upper position. Accordingly, when the actuator 74 is positioned at its upper position, the guide component 60 may be rotated from its position shown in FIG. 16 to its position shown in FIG. 17. Furthermore, when the actuator 74 is positioned at its upper position, the guide component 60 may be rotated from its position shown in FIG. 17 to its position shown in FIG. 16.

Turning again to FIG. 8, the instrument assembly 30 further includes the driver 68. The driver 68 includes a shaft 90. The driver 68 further includes a tip portion 92 attached to the shaft 90 at one end, and a drive portion 94 attached to the shaft 90 at the other end. The drive portion 94 includes a flat drive surface (not shown). The drive portion 94 is configured to be coupled to a chuck of a manual or power drill (not shown). The tip portion 92 includes a drive structure 96. The drive structure 96 includes a plurality of spaced apart linearly extending ribs 98 (see FIG. 8). Note that the coupling component 44 includes a drive structure 100 (see FIGS. 12-13) that is configured to mate with the drive structure 96 of the tip portion 92 when the tip portion 92 is positioned within the passageway 50 of the coupling component 44 as shown in FIG. 8. The drive structure 100 defines a plurality of spaced apart linearly extending slots 102 that is configured to receive respectively the plurality of spaced apart linearly extending ribs 98. It should be appreciated that the slots 102 extend from a proximal end of the coupling component 44 towards the distal end of the coupling component, and terminates prior to arriving at the distal end of the coupling component 44 as shown in FIG. 13. Further, the tip portion 92 of the driver 68 is configured to interact with the structure of the coupling component 44 that defines the slots 102 so that the tip portion 92 of the driver 68 is prevented from being advanced entirely through the passageway 50 of the coupling component 44.

In order to utilize the driver 68 to attach the bone plate 6 to the plate holder 40, the tip portion 92 of the driver needs to be mated with the drive structure 100 of the coupling component 44. To this end, the tip portion 92 is advanced through the guide hole 62A of the guide component 60. As stated above, the handle portion 61 defines a plurality of peripheral slots 63 that are located in the guide hole 62A as shown in FIGS. 5 and 15. In order to advance the tip portion 92 through the guide hole 62A, the plurality of spaced apart ribs 98 of the tip portion are aligned with the plurality of peripheral slots of the handle portion 61. Thereafter, the tip portion 92 is advanced through the guide hole 62A so that the drive structure 96 passes through the peripheral slots 63. Note that the other guide holes 62 of the guide component 60 are not similarly slotted, and are configured to prevent advancement of the tip portion 92 through the guide holes 62. Continued advancement of the tip portion 92 toward the bone plate 6 results in the tip portion 92 being received within the passage 50 of the coupling component 44. When the tip portion 92 is received within the passage 50, the drive structure 96 of the driver 68 is mated with the drive structure 100 of the coupling component 44. When the drive structure 96 of the driver 68 is mated with the drive structure 100 of the coupling component 44, the shaft 90 of the driver 68 extends through the guide hole 62A of the guide component 60.

In order to secure the bone plate 6 to the plate holder 40, the set of external threads 52 of the coupling component 44 of the plate holder 40 are meshingly engaged with the set of internal threads 54 of the bone plate 6. This is accomplished by placing the driver 68 through the guide hole 62A of the guide component 60 and advancing the tip portion 92 of the driver 68 toward the coupling component 44 until the drive structure 96 of the tip portion 92 mates with drive structure 100 of the coupling component 44. Thereafter, the driver 68 is rotated thereby causing the coupling component 44 to be rotated in relation to the bone plate 6. Rotation of the coupling component 44 in relation to the bone plate 6 causes the set of external threads 52 of the coupling component 44 to be meshingly engaged with the set of internal threads 54 of the bone plate 6 thereby securing the bone plate 6 to the plate holder 40.

Figure 25:
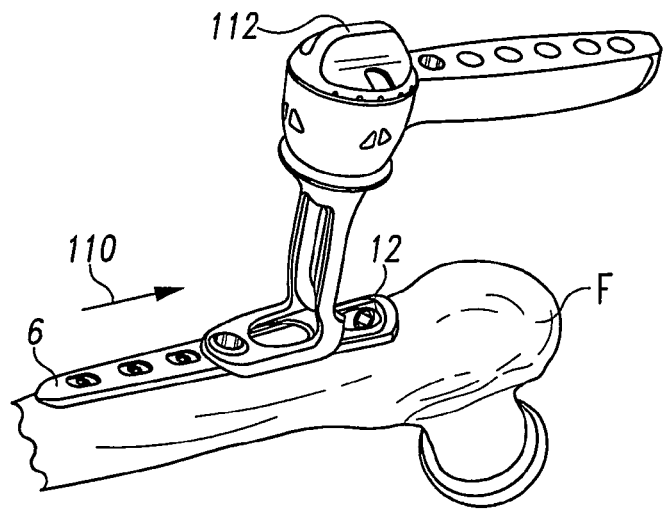
FIG. 25 is a perspective view of the instrument assembly of FIG. 5 (with the implant assembly also shown) and being used to implant the implant assembly in a femur according to the present disclosure, with the femur and the implant assembly being shown removed from the body of a patient P for clarity of viewing (note that the bone plate and fastener guide are shown in an unseated state)
Figure 26:
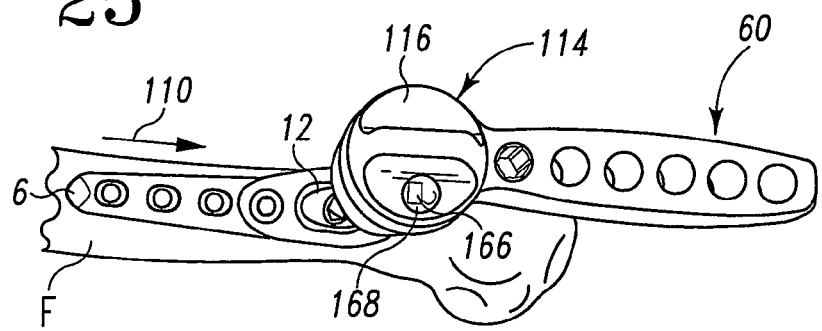
FIG. 26 is another perspective view of the instrument assembly of FIG. 5 (with the implant assembly also shown) and being used to implant the implant assembly in a femur according to the present disclosure, with the femur and the implant assembly being shown removed from the body of a patient P for clarity of viewing (note that the bone plate and fastener guide are shown in a seated state) (also note that the knob 116 is shown in a first position in which the "unlocked" icon is displayed)

After the lag screw assembly 4 is secured within a femoral head, neck, and shaft of the femur F of the patient P as shown in FIG. 4, a surgeon manipulates the plate holder 40 (with the bone plate 6 attached thereto) so that the bone plate 6 is advanced through the incision I to a position on the femur F that is spaced apart from the lag screw assembly 4 as shown in FIG. 25. Thereafter, the plate holder 40 is further manipulated to advance the bone plate 6 in the direction of arrow 110 to a position on the femur F in which the seating surface SS1 of the fastener guide 12 is positioned in contact with the seating surface SS2 of the bone plate 6 as shown in FIG. 26. (See also FIG. 1 showing the bone plate 6 seated against the fastener guide 12.) During such advancement of the bone plate 6 in the direction of arrow 110, the fastener guide 12 is advanced through the access opening 29 defined in the bone plate 6. Further, during such advancement of the bone plate 6 in the direction of arrow 110, the projection 26 of the bone plate 6 is mated with the channel 24 of the fastener guide 12. When the seating surface SS2 of the bone plate 6 is positioned in contact with the seating surface SS1 of the fastener guide 12, the bone plate and the fastener guide are in a seated state (shown in FIG. 26). In contrast, when the seating surface SS2 of the bone plate 6 is spaced apart from the seating surface SS1 of the fastener guide 12, the bone plate and the fastener guide are in an unseated state (shown in FIG. 25).

The instrument assembly 30 is operable to verify whether the bone plate 6 and the fastener guide 12 are in a seated state (i.e. the seating surface SS1 of the fastener guide 12 is located in contact with a seating surface SS2 of the bone plate 6) when the bone plate 6 is attached to the plate holder 40 as shown in FIG. 26. In particular, the instrument assembly 30 includes a stop structure 112 that is movable in relation to the body 42 of the plate holder 40 between an upper position (shown in FIG. 8) and a lower position (shown in FIG. 27). The instrument assembly 30 also includes an actuator 114 that is movable between a first position shown in FIG. 26 to a second position shown in FIG. 28. The actuator 114 includes a knob 116, a shaft 118, a cam 120, and a fastener 122 as shown in FIGS. 8 and 29. The shaft 118 is attached to the knob 116 since the shaft 118 and the knob are integrally molded together as one part. The cam 120 is attached to a distal end of the shaft 118 by the fastener 122. In particular, the cam 120 includes a central passage in which the distal portion of the shaft 118 is positioned. The distal portion of the shaft 118 includes an internally threaded recess. The fastener 122 is threadingly received within the internally threaded recess of the shaft 118 to secure the cam 120 to the shaft 118. When the instrument assembly 30 is assembled as shown in FIG. 8, rotation of the knob 116 causes rotation of the cam 120.

Figure 29:
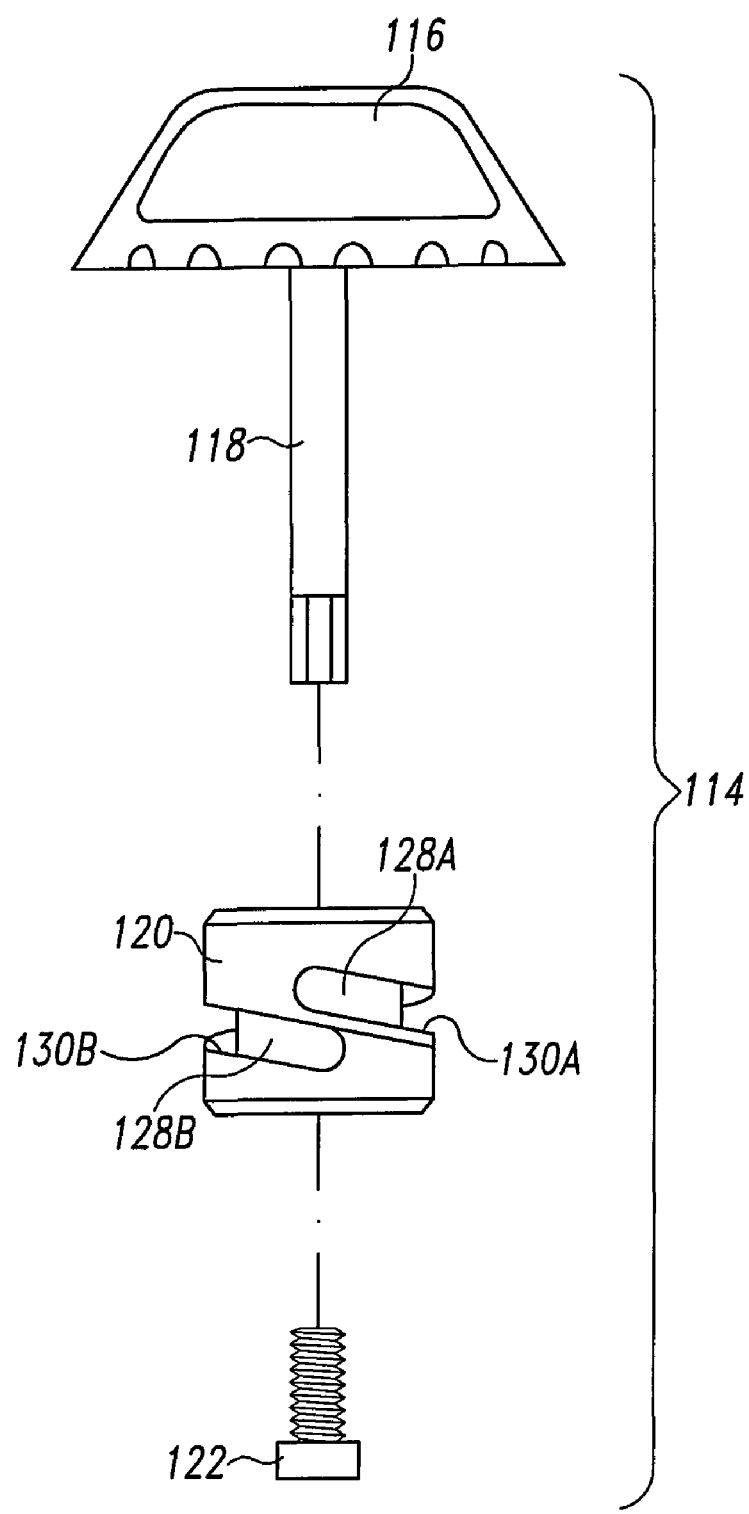
FIG. 29 is an exploded, perspective view of the actuator of the instrument assembly of FIG. 5.
Figure 30:
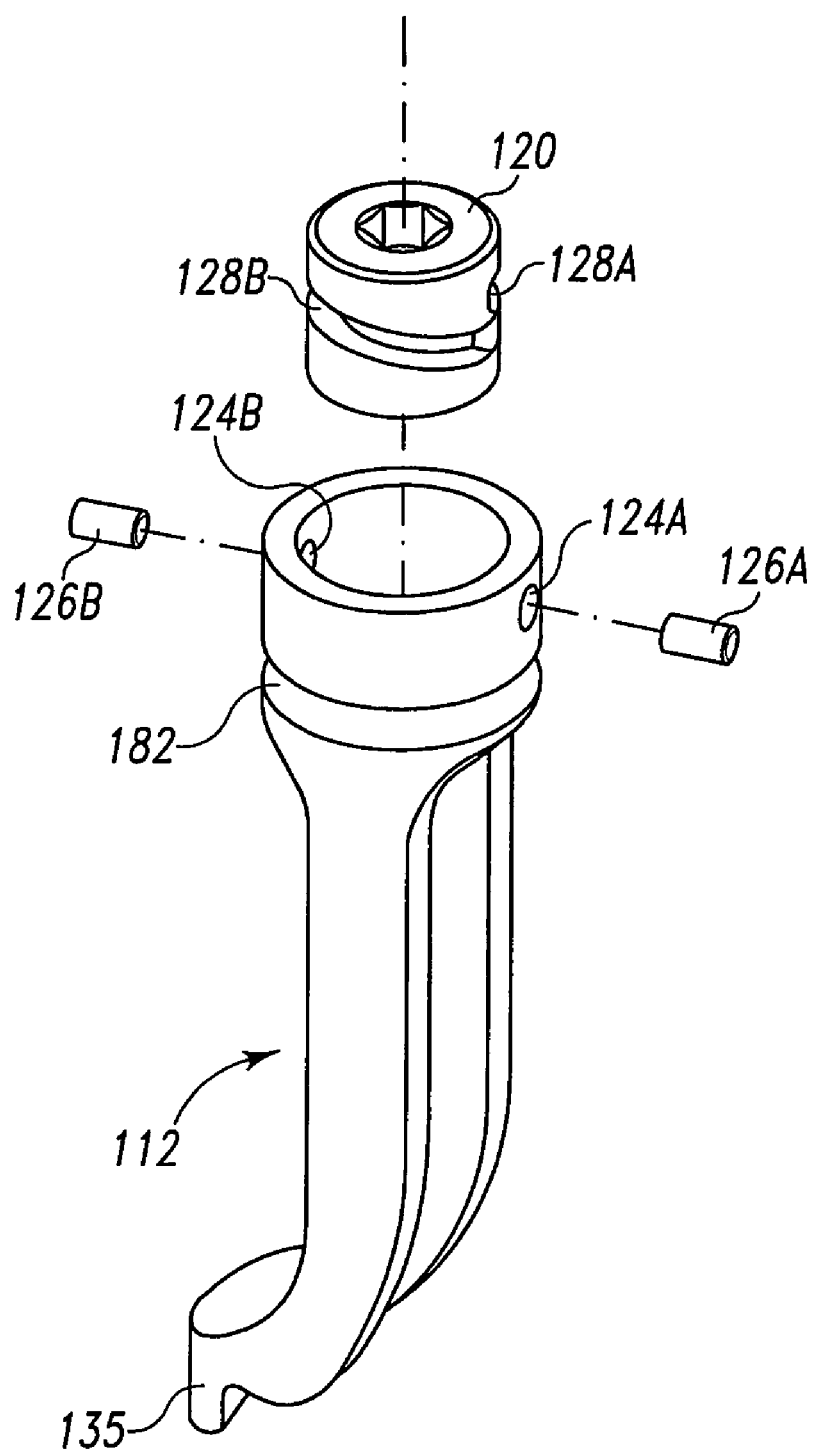
FIG. 30 is an exploded, perspective view of the cam, cam riders, and stop structure of the instrument assembly of FIG. 5.

The stop structure 112 has defined therein a number of holes 124A, 124B as shown in FIG. 30. The stop structure 112 further includes a number of cam riders 126A, 126B each being secured within a respective hole 124A, 124B, yet partially projecting from the respective hole 124A, 124B as shown in FIG. 8. The cam 120 has defined therein a cam track 128A and a cam track 128B. The cam track 128A defines a cam surface 130A, while the cam track 128B defines a cam surface 130B as shown in FIG. 29. When the instrument assembly 30 is assembled, the cam rider 126A is positioned within the cam track 128A and contacts the cam surface 130A, while the cam rider 126B is positioned within the cam track 128B and contacts the cam surface 130B. Rotation of knob 116 causes rotation of the cam 120. In turn, rotation of the cam 120 causes movement of the stop structure 112 in the direction of the axis X due to the interaction between the cam riders 126A, 126B and the cam surfaces 130A, 130B. Rotation of the knob 116 in a clockwise direction causes the stop structure 112 to move downwardly in a path of movement in the direction of the axis X, while rotation of the knob 116 in a counter-clockwise direction causes the stop structure 112 to move upwardly in the path of movement in the direction of the axis X. (See FIG. 8.)

The stop structure 112 includes a tang 135 located at the distal portion thereof. Downward movement of the stop structure 112 in its path of movement from its upper position (shown in FIG. 8) to its lower position (shown in FIG. 27), causes downward movement of the tang 135 from its upper position (shown in solid in FIG. 8) to its lower position (shown in FIG. 27). Note the phantom depiction of the tang 135 in FIG. 8 also shows the tang 135 at its lower position.

It should be appreciated that if the bone plate 6 and the fastener guide 12 were positioned in an unseated state as shown in FIG. 25, downward movement of the stop structure 112 would be prevented due to the presence of the fastener guide 12 in the path of movement of the tang 135 of the stop structure 112. Indeed, the fastener guide 12 would block the downward movement of the stop structure. Thus, if a surgeon is attempting to rotate the knob 116 from its first position (shown in FIG. 26) to its second position (shown in FIG. 28) and rotation of the knob 116 is prevented at some point therebetween, the surgeon would have positive verification that the bone plate 6 and the fastener guide 12 are in an unseated state.

On the other hand, if the bone plate 6 and the fastener guide 12 were positioned in a seated state as shown in FIG. 26, downward movement of the stop structure 112 would be allowed due to the lack of presence of the fastener guide 12 in the path of movement of the tang 135 of the stop structure. Indeed, the fastener guide 12 would not block the downward movement of the stop structure 112 since the fastener guide 12 would be spaced apart from the path of movement of the tang 135. Thus, if a surgeon rotates the knob 116 from its first position (shown in FIG. 26) to its second position (shown in FIG. 28) without complication, the surgeon would have positive verification that the bone plate 6 and the fastener guide 12 are in a seated state.

The knob 116 is rotatable about the axis X as shown in FIG. 8. Rotation of the knob 116 from its first position (shown in FIG. 26) 180° about the axis X to its second position (shown in FIG. 28) causes the stop structure 112 to move from its upper position (shown in FIG. 8) to its lower position (shown in FIG. 27).

Note that after the stop structure 112 is moved to its lower position (shown in FIG. 27), the tang 135 prevents movement of the bone plate 6 in relation to the fastener guide 12. Thus, the stop structure 112 locks the bone plate 6 and the fastener guide 12 in its seated state when the stop structure 112 is positioned in its lower position (shown in FIG. 27).

Figure 28:
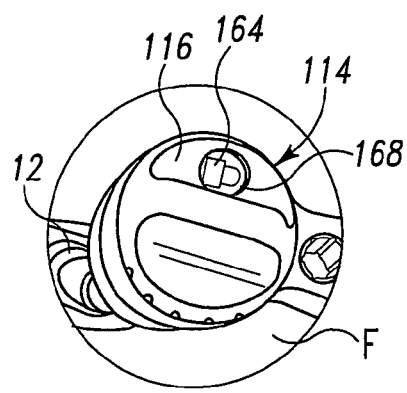
FIG. 28 is an enlarged, fragmentary, perspective view of the instrument assembly of FIG. 5 showing the knob 116 in a second position in which the "locked" icon is displayed.
Figure 31:
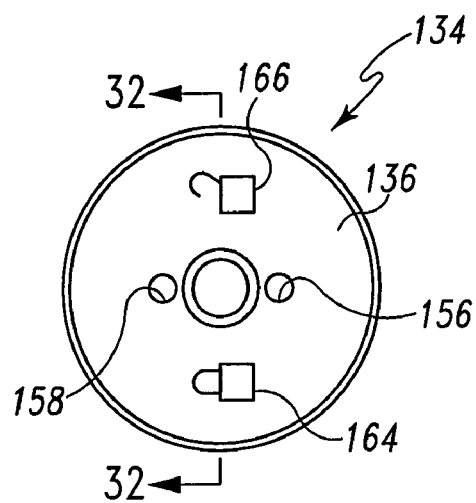
FIG. 31 is a top elevational view of the support member of the instrument assembly of FIG. 5.
Figure 32:
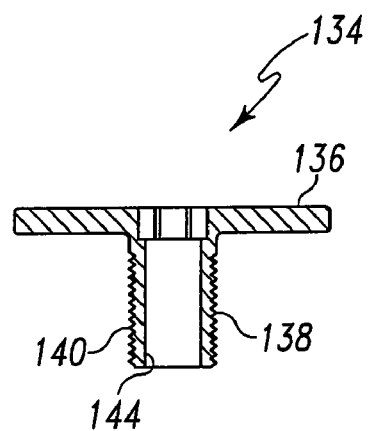
FIG. 32 is a cross sectional view of the support member taken along the line 32-32 of FIG. 31.

The instrument assembly 30 is configured to generate a tactile and audible indication of when the stop structure 112 is located at its upper position (shown in FIG. 26) and at its lower position (shown in FIG. 28). In particular, the instrument assembly 30 further includes a support member 134 that includes an upper portion 136 and a lower portion 138 as shown in FIGS. 31-32. (See also FIG. 8.) The lower portion 138 includes a set of external threads 140 that mate with a set of internal thread 142 defined in the neck 43 of the plate holder 40 as shown in FIG. 8. The support member 134 defines a passage 144 through which the shaft 118 of the actuator 114 extends. A sleeve 146 is positioned within the cavity 66 and surrounds both the neck 43 of the plate holder 40 and the lower portion 138 of the support member 134 as shown in FIG. 8.

Figure 33:
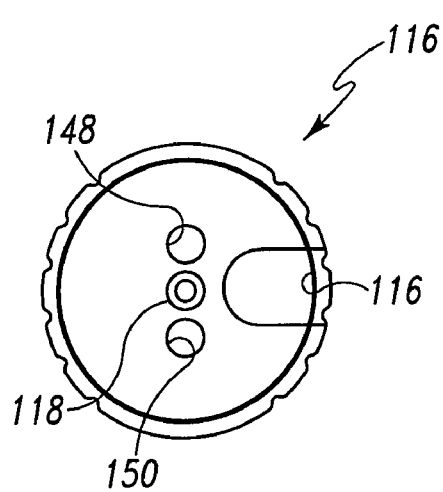
FIG. 33 is a bottom elevational view of the knob of the actuator of FIG. 29.
Figure 34:
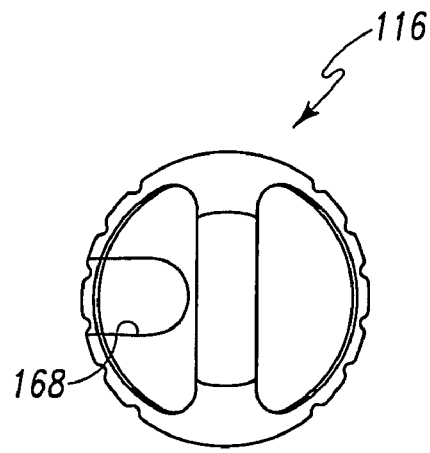
FIG. 34 is a top elevational view of the knob of the actuator of FIG. 29.

The knob 116 includes a spring recess 148 and a spring recess 150 as shown in FIGS. 33-34. A spring 152 is positioned in the spring recess 148, while a spring 154 is positioned in the spring recess 150. (See FIG. 5.) The upper portion 138 of the support member 134 has defined therein a detent recess 156 and a detent recess 158 as shown in FIGS. 31-32.

When the knob 116 is positioned in its first position (shown in FIG. 26), a ball detent 160 is interposed between the spring 152 and the detent recess 156 thereby resulting in the ball detent 160 being urged into the detent recess 156 as shown in FIG. 8. Similarly, when the knob 116 is positioned in its first position (shown in FIG. 26), a ball detent 162 is interposed between the spring 154 and the detent recess 158 thereby resulting in the ball detent 162 being urged into the detent recess 158 as shown in FIG. 8.

While the knob 116 is being rotated from its first position (shown in FIG. 26) to its second position (shown in FIG. 28), the ball detent 160 is advanced out of the detent recess 156 and is interposed between the spring 152 and the support member 134. Similarly, while the knob 116 is being rotated from its first position (shown in FIG. 26) to its second position (shown in FIG. 28), the ball detent 162 is advanced out of the detent recess 158 and is interposed between the spring 154 and the support member 134.

Then, when the knob 116 arrives so as to be positioned at its second position (shown in FIG. 28), the ball detent 160 becomes interposed between the spring 152 and the detent recess 158 thereby resulting in the ball detent 160 being urged into the detent recess 158. Similarly, when the knob 116 is positioned at its second position (shown in FIG. 26), the ball detent 162 becomes interposed between the spring 154 and the detent recess 156 thereby resulting in the ball detent 162 being urged into the detent recess 156.

Figure 27:
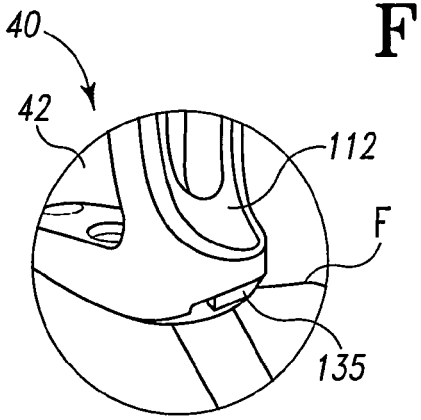
FIG. 27 is an enlarged, fragmentary, perspective view of the instrument assembly of FIG. 5, however, the stop structure 112 is shown positioned in its lower position.

When the knob 116 arrives so as to be positioned at its second position (shown in FIG. 28), a click sound is heard by the surgeon indicating that the stop structure 112 is now positioned at its lower position shown in FIG. 27. Similarly, when the surgeon rotates the knob 116 back to its first position (shown in FIG. 26) from its second position (shown in FIG. 28), arrival of the knob 116 at its first position (shown in FIG. 26) results in a similar click sound being heard by the surgeon. The click sounds are caused by the ball detents 160, 162 being urged into their respective detent recesses 156, 158 by their respective springs 152, 154.

In addition, the instrument assembly 30 is configured to provide a visual indication of when the stop structure 112 is located at its upper position (shown in FIG. 26) and at its lower position (shown in FIG. 28). In particular, the support member 134 includes a "locked" icon 164 and an "unlocked" icon 166 located on an upper surface of the upper portion 136 of the support member 134 as shown in FIG. 31. (See also FIG. 6.) The icons 164, 166 are preferably etched into an upper surface of the upper portion 136 of the support member 134. The icon 164 is preferably colored red, while the icon 166 is preferably colored green. Of course, other color schemes may be used. The knob 116 has defined therein a viewing opening 168 as shown in FIGS. 33-34. As shown in FIG. 26, when the knob 116 is positioned in its first position, the viewing opening 168 is positioned over the "unlocked" icon 166 thereby displaying the "unlocked" icon to the surgeon which informs the surgeon the stop structure 112 is now positioned at its upper position. On the other hand, as shown in FIG. 28, when the knob 116 is positioned in its second position, the viewing opening 168 is positioned over the "locked" icon 164 thereby displaying the "locked" icon to the surgeon which informs the surgeon the stop structure 112 is now positioned at its lower position.

Furthermore, the instrument assembly 30 is configured to provide an additional visual indication of when the stop structure 112 is located at its upper position (shown in FIG. 26) and at its lower position (shown in FIG. 28). In particular, the body 42 of the plate holder 40 has defined therein a number of viewing holes 180 as shown in FIGS. 9-10. The stop structure 112 defines a groove 182 that extends in a circumferential manner around the stop structure as shown in FIG. 30. The groove 182 is preferably colored red. Of course, the groove may be colored with a color other than red, such as yellow, pink, or orange. When the stop structure 112 is located at its upper position (shown in FIG. 26), the red-colored groove 182 of the stop structure 112 is hidden from view of a user of the instrument assembly 30 since the red-colored groove 182 is (i) located within the neck 43 of the body 42 of the plate holder 40, and (ii) located proximal to the viewing opening 180 defined in the body 42 of the plate holder 40. (See, e.g., FIG. 8, as well as, FIG. 7.) In contrast, when the stop structure 112 is located at its lower position (shown in FIG. 28), the red-colored groove 182 of the stop structure 112 is exposed to a user of the instrument assembly 30 since the red-colored groove is (i) located distal to the neck 43 of the body 42 of the plate holder 40, and (ii) aligned with the viewing openings 180 defined in the body 42 of the plate holder 40. (See, e.g., FIGS. 7 and 8.)

Thus, when the knob 116 is positioned in its first position as shown in FIGS. 8 and 26, the red-colored groove 182 is hidden from view thereby informing the surgeon the stop structure 112 is now positioned at its upper position. On the other hand, as shown in FIG. 28, when the knob 116 is positioned in its second position, the red-colored groove 182 is exposed to a user of the instrument assembly 30 which informs the surgeon the stop structure 112 is now positioned at its lower position.

Use of Instrumentation and Implant Components

Figure 35:
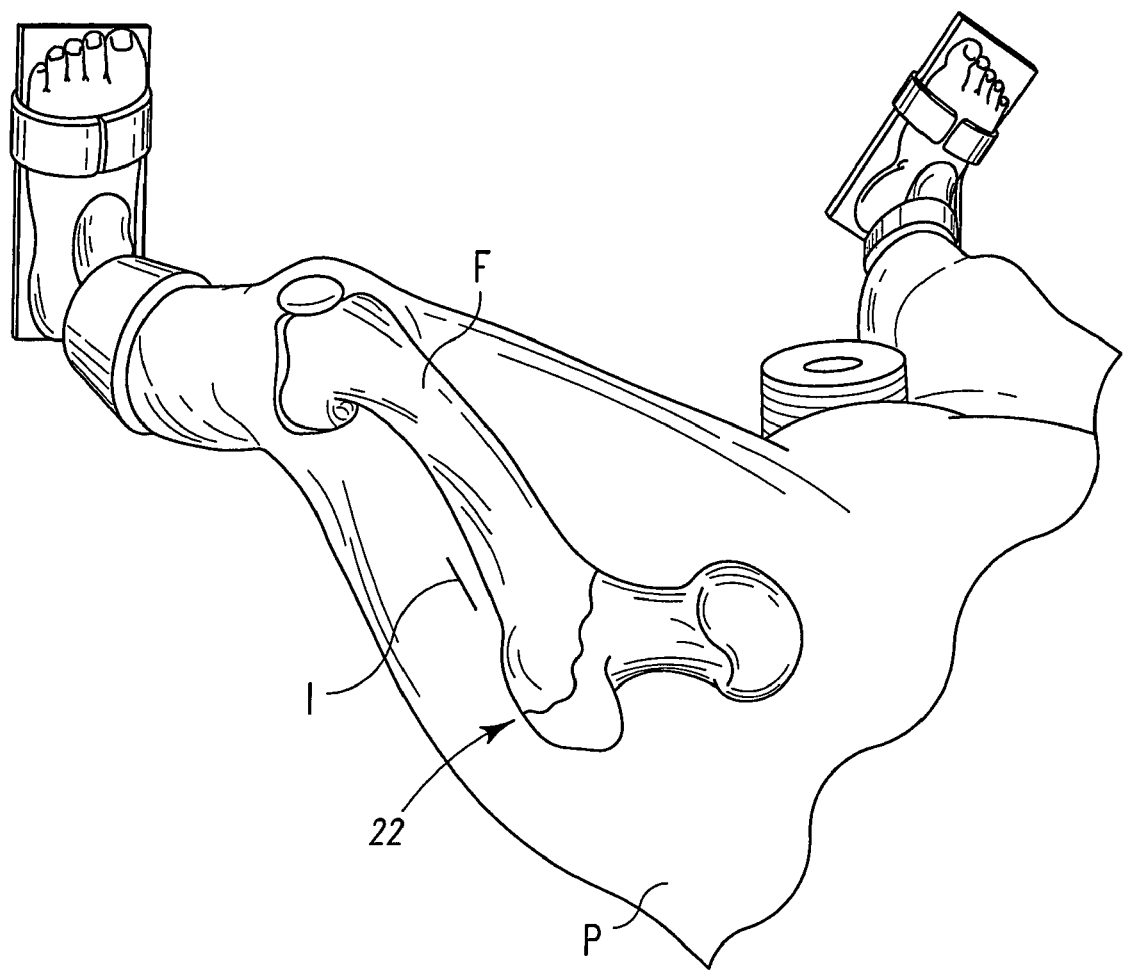
FIG. 35 is a fragmentary, perspective view of a patient with a fractured femur.

Use of the instrumentation and implant components described above facilitate reduction of a hip fracture in a minimally invasive manner. In particular, in order to perform such a procedure, a patient P is placed in a supine position on a standard fracture table. The fracture is then reduced and aligned using traction with external rotation followed by approximately 20 degrees of internal rotation to compress the fracture 22 (see FIG. 35). The reduction is then verified using dual-plane image intensification. The hip is then prepared and draped in a conventional manner.

Thereafter, an incision I is made that is 3-8 cm long (depending on the length of the bone plate being used) in the lateral aspect of the hip, with dissection beginning distal to the flare of the greater trochanter down to the vastus ridge and extending distally. (See FIG. 35.) The dissection is carried sharply down through the skin and subcutaneous tissue to the fascia lata. The fascia lata is split longitudinally thereby exposing the vastus lateralis. The vastus lateralis is then retracted anteriorly and the lateral aspect of the femoral shaft is then exposed.

A guide wire (e.g. a 3.2 mm guide wire) (not shown) is exteriorly placed adjacent to the femoral neck to assess lateral positioning and neck angle. The guide wire is then advanced into the shaft, neck, and head of the femur F of the patient P. The guide wire is advanced under image intensification until its threads are secure to subchondral bone in the center of the femoral head in both anterior-posterior and lateral views.

Thereafter, a lag screw drill (not shown) is advanced over the guide wire (under radiography) and into the femur F to create a fastener cavity (not shown). Upon completion of the fastener cavity, the lag screw drill is removed from the femur F, leaving the guide wire in place. The lag screw assembly 4 is then advanced into the fastener cavity with the lag screw component 14 being advanced over the guide wire. The lag screw assembly 4 is secured to the femur F by rotating the lag screw 10 with a driver tool (not shown) until the lag screw assembly 4 assumes a position in relation to the femur F as shown in FIG. 4.

Once the lag screw assembly 4 has been secured within the femur as shown in FIG. 4, the bone plate 6 may be assembled to the fastener guide or barrel 12. This is accomplished with the assistance of the instrument assembly 30. In particular, using the instrument assembly 30 having the bone plate 6 attached thereto (as described above), the bone plate 6 is advanced through the incision I. After being advanced through the incision I, the bone plate 6 is advanced distally until the proximal end of the bone plate 6 is located distal to the lag screw assembly 4 as shown in FIG. 25. The bone plate 6 is then slid toward the lag screw assembly 4 so that the fastener guide 12 is passed through the access opening 29 defined in the proximal end of the bone plate 6. Also during sliding of the bone plate 6 toward the lag screw assembly 4, the projection 26 of the bone plate 6 advances into the channel 24 of the fastener guide 12. Continued advancement of the bone plate 6 in relation to the fastener guide 12 results in the seating surface SS1 of the fastener guide 12 contacting the seating surface SS2 of the bone plate 6 as shown in FIG. 26. When seating surface SS1 is in contact with the seating surface SS2, the bone plate 6 and the fastener guide 12 are in an assembled state.

During the above-described advancement of the bone plate 6 relative to the fastener guide 12, the stop structure 112 of the instrument assembly 30 is located in its upper position. When the stop structure 112 is in its upper position, the knob 116 of the actuator 114 of the instrument assembly 30 is located at its first position (shown in FIG. 26) such that the "unlocked" icon 166 is visible through the viewing opening 168 of the knob 116.

When the surgeon believes the bone plate 6 has been advanced into its assembled state with the fastener guide 12, the surgeon rotates the knob 116 clockwise so that the viewing opening 168 is moved to a second position (shown in FIG. 28) in which the viewing opening 168 is aligned with "locked" icon 164 thereby displaying the "locked" icon 164 through the viewing opening 168. If the knob 116 is prevented from moving to from its first position (shown in FIG. 26) to its second position (shown in FIG. 28), the surgeon is positively notified the bone plate 6 and the fastener guide 12 are not in an assembled state. Thus, the surgeon would need to further mate the bone plate 6 and the fastener guide 12 so that the seating surface SS1 of the fastener guide 12 is positioned in contact with the seating surface SS2 of the bone plate 6. On the other hand, if the knob 116 is allowed to move from its first position (shown in FIG. 26) to its second position (shown in FIG. 28), then a surgeon is positively notified the bone plate 6 and the fastener guide 12 are in their assembled state. When the knob 116 is positioned at its second position (shown in FIG. 28), the stop structure 112 is located at its lower position thereby retaining or locking the bone plate 6 and the fastener guide 12 in their assembled state.

If desired, prior to moving the knob 116 from its first position ("unlocked" icon displayed and red-colored groove 182 hidden from view) to its second position ("locked" icon displayed and red-colored groove 182 exposed to a user), the bone plate 6 may be impacted with an impactor 170 as shown in FIG. 17. In particular, the impactor 170 is manipulated until its distal end is received within an impactor recess 172 of the plate holder 40. Thereafter, the proximal end of the impactor 170 is tapped firmly several times (e.g. three or four) with a mallet (not shown) to transmit force to the bone plate 6 thereby ensuring the bone plate 6 and the lag screw assembly 4 are fully mated.

When the knob 116 is positioned at its second position (shown in FIG. 28), indicating that the bone plate 6 and the fastener guide 12 are in their assembled state, the guide component 60 is moved from its position shown in FIG. 17 to its position shown in FIG. 16. This is accomplished by moving the actuator 74 from its lower position (shown in solid in FIG. 8) to its upper position (shown in phantom in FIG. 8), and thereafter rotating the guide component 180° about the axis X (see FIG. 8) from its position shown in FIG. 17 to its position shown in FIG. 16. Upon arriving at its position shown in FIG. 16, the guide component 60 becomes locked in relation to plate holder 40. At this position, the guide holes 62, 62A of the guide component 60 are respectively aligned with the fastener openings 7, 7A of the bone plate 6.

With the guide component 60 secured in its position shown in FIG. 16 (see also FIG. 8), instruments such as the drill assembly 70 may be advanced through the guide holes 62, 62A and the fastener openings 7, 7A to create fastener cavities (not shown) in the femur that are aligned with the fastener openings 7, 7A. Thereafter, the bone screws 8A, 8B (such as 4.5 mm bone screws) are driven through the fastener openings 7, 7A of the bone plate 6 and into the shaft of the femur F. The bone screws 8A, 8B are driven (one at a time) through an outer sheath S that respectively extends through the guide holes 62, 62A in the guide component. (See, e.g., FIG. 8.)

After placement of the final bone screw 8A, 8B, the driver 68 is advanced through the guide hole 62A of the guide component 60 until the drive structure 96 of the tip portion 92 of the driver mates with drive structure 100 of the coupling component 44. Thereafter, the driver 68 is rotated in the counter-clockwise direction thereby causing the coupling component 44 to be rotated in relation to the bone plate 6. Rotation of the coupling component 44 in relation to the bone plate 6 in the counter-clockwise direction causes the set of external threads 52 of the coupling component 44 to become meshingly disengaged with the set of internal threads 54 of the bone plate 6 thereby detaching (or unlocking) the plate holder 40 from the implanted bone plate 6. Thereafter, the plate holder 40 is removed from the patient P through the incision, and the incision I is closed in a conventional manner.

There is a plurality of advantages arising from the various features of each of the embodiments of the assembly described herein. It will be noted that alternative embodiments of the assembly may not include all of the features described yet still benefit from at least some of the advantages of such features. Those of ordinary skill in the art may readily devise their own implementations of the assembly that incorporates one or more of the features and fall within the spirit and scope of the present invention as defined by the appended claims.

What is claimed is:

1. An assembly, comprising:
a plate holder having a body;
a stop structure movable in relation to said body between a first location and a second location; and
an actuator movable between a first position and a second position,
wherein movement of said actuator from said first position to said second position causes movement of said stop structure from said first location to said second location,
further comprising a support member that includes (i) a first visual indicator, and (ii) a second visual indicator that is spaced apart from said first visual indicator,
wherein said actuator further includes a knob positioned adjacent to said support member,
wherein said actuator defines a viewing opening,
wherein said viewing opening is aligned with said first visual indicator when said actuator is positioned at said first position,
wherein said viewing opening is aligned with said second visual indicator when said actuator is positioned at said second position,
further comprising a bone plate assembly including (i) a bone plate having a plurality of fastener openings defined therein, said bone plate being attached to said body, and (ii) a fastener guide,
wherein one of said bone plate and said fastener guide includes a channel,
wherein the other of said bone plate and said fastener guide includes a projection configured to be received in said channel,
wherein said bone plate includes a first seating surface,
wherein said fastener guide includes a second seating surface,
wherein, when said projection is received within said channel, said bone plate assembly is positionable between a seated state and an unseated state,
wherein, when said bone plate assembly is in said seated state, said second seating surface is positioned in contact with said first seating surface,
wherein, when said bone plate assembly is in said unseated state, said second seating surface is spaced apart from said first seating surface,
wherein, said stop structure defines a path of movement from said first location to said second location,
wherein, when said bone plate assembly is in said unseated state, said fastener guide is positioned in said path of movement of said stop structure, and
wherein, when said bone plate assembly is in said seated state, said fastener guide is spaced apart from said path of movement of said stop structure.

2. The assembly of claim 1, wherein said bone plate assembly further includes a fastener at least partially positioned within said fastener guide.

3. An assembly, comprising:
a plate holder having a body;
a stop structure movable in relation to said body between a first location and a second location; and
an actuator movable between a first position and a second position,
wherein movement of said actuator from said first position to said second position causes movement of said stop structure from said first location to said second location,
wherein:
said actuator includes a cam, and
movement of said cam causes movement of said stop structure, and
wherein:
said actuator further includes (i) a knob, and (ii) a shaft attached to said knob,
said shaft is further attached to said cam, and
rotation of said knob causes rotation of said cam,
further comprising (i) a support member attached to said plate holder, (ii) a detent, and (iii) a spring, wherein:
said support member defines a first aperture and a second aperture,
said detent is interposed between said support member and said knob,
said spring is interposed between said detent and said knob,
said detent is positioned in said first aperture when said actuator is positioned at said first position, and
said detent is positioned in said second aperture when said actuator is positioned at said second position.

4. An assembly, comprising:
a plate holder having a body;
a stop structure movable in relation to said body between a first location and a second location; and
a bone plate assembly including (i) a bone plate having a plurality of fastener openings defined therein, said bone plate being attached to said body, and (ii) a fastener guide,
wherein one of said bone plate and said fastener guide includes a channel,
wherein the other of said bone plate and said fastener guide includes a projection configured to be received in said channel,
wherein:
said bone plate includes a first seating surface,
said fastener guide includes a second seating surface,
when said projection is received within said channel, said bone plate assembly is positionable between a seated state and an unseated state, when said bone plate assembly is in said seated state, said second seating surface is positioned in contact with said first seating surface, when said bone plate assembly is in said unseated state, said second seating surface is spaced apart from said first seating surface, said stop structure defines a path of movement from said first location to said second location, when said bone plate assembly is in said unseated state, said fastener guide is positioned in said path of movement of said stop structure, and when said bone plate assembly is in said seated state, said fastener guide is spaced apart from said path of movement of said stop structure, wherein said assembly further comprises an actuator configured to move said stop structure between said first location and said second location, and wherein said actuator includes a cam, and movement of said cam causes movement of said stop structure.

5. The assembly of claim 4, wherein said bone plate assembly further includes a fastener at least partially positioned within said fastener guide.

6. The assembly of claim 4, wherein:
said actuator further includes (i) a knob, and (ii) a shaft attached to said knob,
said shaft is further attached to said cam, and
rotation of said knob causes rotation of said cam.

7. The assembly of claim 6, further comprising (i) a support member attached to said plate holder, (ii) a detent, and (iii) a spring, wherein:
said support member defines a first aperture and a second aperture,
said detent is interposed between said support member and said knob,
said spring is interposed between said detent and said knob,
said detent is positioned in said first aperture when said stop structure is positioned at said first location, and
said detent is positioned in said second aperture when said stop structure is positioned at said second location.

8. The assembly of claim 7, wherein:
said knob is rotatable about an axis, and
rotation of said knob 180° about said axis causes movement of said stop structure from said first location to said second location.

9. The assembly of claim 4, further comprising a guide component attached to said plate holder, said guide component having a plurality of guide holes defined therein.

10. The assembly of claim 9, wherein said guide component includes a handle portion having said plurality of guide holes defined therein.

11. The assembly of claim 4, further comprising a support member that includes (i) a first indicator, and (ii) a second indicator that is spaced apart from said first indicator, wherein:
said actuator further includes a knob positioned adjacent to said support member,
said actuator defines a viewing opening,
said viewing opening is aligned with said first indicator when said actuator is positioned at said first position, and
said viewing opening is aligned with said second indicator when said actuator is positioned at said second position.

12. The assembly of claim 4, wherein:
said body of said plate holder defines a viewing hole,
said stop structure includes a visual indicator,
said viewing hole is aligned with said visual indicator when said actuator is positioned at said second position, and
said viewing hole is misaligned with said visual indicator when said actuator is positioned at said first position.

\* \* \* \* \*

UNITED STATES PATENT AND TRADEMARK OFFICE
CERTIFICATE OF CORRECTION

| | | |
|---|---|---|
| PATENT NO. | : 7,837,689 B2 | Page 1 of 1 |
| APPLICATION NO. | : 11/904504 | |
| DATED | : November 23, 2010 | |
| INVENTOR(S) | : Matthew V. Leyden et al. | |

It is certified that error appears in the above-identified patent and that said Letters Patent is hereby corrected as shown below:

Column 2,
Line 51, after "FIG. 3D" delete "." and insert --;--

Column 2,
Line 55, after "patient" delete "." and insert --;--

Column 3,
Line 13, after "FIG. 14" delete "." and insert --;--

Column 8,
Line 9, replace "able slide" with --able to slide--

Column 11,
Line 34, replace "thread" with --threads--

Column 14,
Line 20, after "moving" delete "to"

Column 18,
Line 5, replace "of claim 7" with --of claim 6--

Signed and Sealed this
Nineteenth Day of February, 2013

Teresa Stanek Rea
*Acting Director of the United States Patent and Trademark Office*